United States Patent
Greenwald et al.

(10) Patent No.: US 6,720,306 B2
(45) Date of Patent: Apr. 13, 2004

(54) TETRAPARTATE PRODRUGS

(75) Inventors: Richard B. Greenwald, Somerset, NJ (US); Hong Zhao, Edison, NJ (US)

(73) Assignee: Enzon Pharmaceuticals, Inc., Bridgewater, NJ (US)

(*) Notice: Subject to any disclaimer, the term of this patent is extended or adjusted under 35 U.S.C. 154(b) by 0 days.

(21) Appl. No.: 09/758,993

(22) Filed: Jan. 12, 2001

(65) Prior Publication Data

US 2001/0031873 A1 Oct. 18, 2001

Related U.S. Application Data

(63) Continuation-in-part of application No. 09/183,557, filed on Oct. 30, 1998, now Pat. No. 6,180,095, which is a continuation-in-part of application No. 08/992,435, filed on Dec. 17, 1997, now abandoned.

(51) Int. Cl.[7] ................... A61K 31/196; A61K 31/704; A61K 38/03; C07H 15/252; C07K 5/103

(52) U.S. Cl. ............................... 514/18; 514/2; 514/34; 514/49; 514/512; 514/547; 514/564; 530/330; 530/331; 530/345; 536/6.4; 536/28.5; 558/273; 560/159; 560/165; 562/449

(58) Field of Search .................. 560/157, 158, 560/159, 160, 165, 179, 186, 187; 526/332; 528/421; 558/273; 562/449; 536/4.1, 6.4, 168, 172, 181, 28.5; 514/2, 13, 18, 84, 49, 347, 345, 351, 353, 434, 425, 426, 432, 445, 497, 457, 460, 471, 472, 473, 480, 512, 547, 564; 424/35.1, 35.2, 83.4, 94.3; 530/336, 330, 331, 345, 351, 403, 409, 410; 435/188

(56) References Cited

U.S. PATENT DOCUMENTS

| | | | |
|---|---|---|---|
| 4,179,337 A | 12/1979 | Davis et al. ................ 435/181 |
| 5,093,531 A | 3/1992 | Sano et al. ................. 568/337 |
| 5,122,614 A | 6/1992 | Zalipsky ..................... 548/520 |
| 5,321,095 A | 6/1994 | Greenwald ................. 525/404 |
| 5,349,001 A | 9/1994 | Greenwald et al. ........ 525/408 |
| 5,382,657 A | 1/1995 | Karasiewicz et al. ...... 530/351 |
| 5,561,119 A | 10/1996 | Jacquesy et al. ........... 514/34 |
| 5,569,720 A | 10/1996 | Mongelli et al. .......... 525/329.4 |
| 5,605,976 A | 2/1997 | Martinez et al. ............ 525/408 |
| 5,614,549 A | 3/1997 | Greenwald et al. ......... 514/449 |
| 5,643,575 A | 7/1997 | Martinez et al. ......... 424/194.1 |
| 5,672,584 A | 9/1997 | Borchardt et al. ............ 514/11 |
| 5,710,135 A | 1/1998 | Leenders et al. ............. 514/34 |
| 5,840,900 A | 11/1998 | Greenwald et al. .......... 546/48 |
| 5,877,158 A * | 3/1999 | Bosslet et al. ................. 514/34 |
| 5,965,119 A | 10/1999 | Greenwald et al. ...... 424/78.37 |
| 6,180,095 B1 * | 1/2001 | Greenwald et al. ........ 424/85.1 |

FOREIGN PATENT DOCUMENTS

| | | |
|---|---|---|
| WO | WO 96/22277 | 7/1996 |
| WO | WO 98/13059 | 4/1998 |
| WO | WO 01/09139 A1 | 2/2001 |

OTHER PUBLICATIONS

Greenwald, Richard B., et al. Drug Delivery Systems Employing 1,4—or 1,6—Elimination: Poly (ethylene–glycol) Prodrugs of Amine–Containing Compounds, Journal of Medicinal Chemistry, vol. 42, No. 18, pp. 3657–3667, 1999.

Maeda, H., et al., "Tumor vascular permeability and the EPR effect in macromolecular therapeutics: a review" J. Contr. Release 65 (2000) pp. 271–284.

Zier et al. Polyethylene Glycol Bound Benzyl and Fluorenyl Derivatives . . . Tetrahedron Letters, vol. 35, No. 7, pp. 1039–1042 (1994).

Record of Invention "2– and 4– Hydroxybenzyl Alcohol–Containing Linkers", Zalipsky, Nov. 18, 1991.

Declaration under 37 C.F.R. 1.132 of Richard B. Greenwald including Exhibits 1 and 2, Sep. 8, 1999.

Declaration under 37 C.F.R. 1.132 of Jeffrey McGuire, Sep. 8, 1999.

Shearwater Polymers, Inc., *Catalog—Polyethylene Glycol Derivatives, 1997–1998*; p. 8.

Leenders, R.G.G.et al., *Highly Diastereoselective Synthesis of Anomeric B–O–Glycopyranosyl Carbamates from Isocyanates*, Synthesis Nov. 1996; pp 1309–1312.

Leenders, R.G.G. et al. *B–Glucuronyl Carbamate Based Pro–moieties Designed for Prodrugs in ADEPT*, 1995; Tetrahedron Letters vol. 36, No. 10 pp. 1701–1704.

Waldmann, H. et al, *Synthesis of the Palmitoylated and Farnesylated C–Terminal Lipohexapeptide of the Human N–Ras Protein by Employing . . .* , Angew. Chem Int. Ed. 1995, 34 No. 20 ; pp. 2259–2262.

Jungheim, L.N. et al., *Design of Antitumor Prodrugs: Substrates for Antibody Targeted Enzymes*, Chem. Rev. 1994; 94 pp. 1553–1566.

Bundgaard, H. *The Double Prodrug Concept and its Applications*, Advanced Drug Delivery Reviews, 3 1989 pp. 39–65.

Wakselman, M. et al., *An Alkali–labile Substituted Benzyloxycarbonyl Amino–protecting Group*, JCS Chem. Comm1973; pp. 593–594.

Carl, P.L., et al. *A Novel Connector Linkage Applicable in Prodrug Design*, Journal of Medicinal Chemistry, vol. 24, No. 5 (May 1981).

Shan, D., et al., Prodrug Strategies Based on Intramolecular Cyclization Reactions, Journal of Pharmaceutical Sciences, Jul. 1997, vol. 86, No. 7, pp765–767.

* cited by examiner

*Primary Examiner*—Jeffrey E. Russel
(74) *Attorney, Agent, or Firm*—Muserlian, Lucas & Mercanti, LLP

(57) ABSTRACT

A compound of Formula I, providing tetrapartate prodrugs is provided (I)

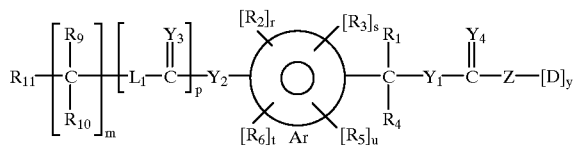

wherein:
- $L_1$ is a bifunctional linking moiety;
- D is a moiety that is a leaving group, or a residue of a compound to be delivered into a cell;
- Z is covalently linked to $[D]_y$, wherein Z is selected from the group consisting of: a moiety that is actively transported into a target cell, a hydrophobic moiety, and combinations thereof,
- $Y_1$, $Y_2$, $Y_3$ and $Y_4$ are each independently O, S, or $NR_{12}$;
- $R_{11}$ is a mono- or divalent polymer residue;
- $R_1$, $R_4$, $R_9$, $R_{10}$ and $R_{12}$ are independently selected from the group consisting of hydrogen, $C_{1-6}$ alkyls, $C_{3-12}$ branched alkyls, $C_{3-8}$ cycloalkyls, $C_{1-6}$ substituted alkyls, $C_{3-8}$ substituted cycloalkyls, aryls, substituted aryls, aralkyls, $C_{1-6}$ heteroalkyls and substituted $C_{1-6}$ heteroalkyls;
- $R_2$, $R_3$, $R_5$ and $R_6$ are independently selected from the group consisting of hydrogen, $C_{1-6}$ alkyls, $C_{1-6}$ alkoxy, phenoxy, $C_{1-8}$ heteroalkyls, $C_{1-8}$ heteroalkoxy, substituted $C_{1-6}$ alkyls, $C_{3-8}$ cycloalkyls, $C_{3-8}$ substituted cycloalkyls, aryls, substituted aryls, aralkyls, halo-, nitro- and cyano-, carboxy-, $C_{1-6}$ carboxyalkyls and $C_{1-6}$ alkylcarbonyls;
- Ar is a moiety which when included in Formula (I) forms a multi-substituted aromatic hydrocarbon or a multi-substituted heterocyclic group;
- (m), (r), (s), (t), and (u) are independently zero or one;
- (p) is zero or a positive integer; and (y) is 1 or 2;

together with methods of preparing and using these new tetrapartate prodrugs.

35 Claims, 9 Drawing Sheets

TETRAPARTATE PRODRUGS

CROSS REFERENCE TO RELATED APPLICATIONS

This application is a continuation-in-part of U.S. patent application Ser. No. 09/183,557, filed on Oct. 30, 1998, now U.S. Pat. No. 6,180,095 which in turn is a continuation-in-part of U.S. patent application Ser. No. 08/992,435, filed on Dec. 17, 1997, now abandoned, the contents of both of which are incorporated herein by reference.

TECHNICAL FIELD

The present invention relates to tetrapartate prodrugs. In particular, the invention relates to polymer conjugates that provide tetrapartate prodrugs that deliver active agents linked to uptake enhancing moieties effective to provide enhanced efficacy, e.g., as antitumor agents or the like.

BACKGROUND OF THE INVENTION

Over the years, several methods of administering biologically-effective materials to mammals have been proposed. Many biologically-effective materials, e.g., including medicinal agents and the like, are available as water-soluble salts and can be included in pharmaceutical formulations relatively easily. Problems arise when the desired biologically-effective material is either insoluble in aqueous fluids or is rapidly degraded in vivo. For example, alkaloids are often especially difficult to solubilize.

One way to solubilize biologically-effective material(s) is to include them as part of a soluble prodrug. Thus, prodrugs include chemical derivatives of a biologically-active material, or parent compound which, upon administration, eventually liberate the parent compound in vivo. Prodrugs allow the artisan to modify the onset and/or duration of action of an agent in vivo and can modify the transportation, distribution or solubility of a drug in the body. Furthermore, prodrug formulations often reduce the toxicity and/or otherwise overcome difficulties encountered when administering pharmaceutical preparations.

Typical examples of prodrugs include organic phosphates or esters of alcohols or thioalcohols. See *Remington's Pharmaceutical Sciences*, 16th Ed., A. Osol, Ed. (1980), the disclosure of which is incorporated by reference herein.

Prodrugs are, by definition, forms of the parent or active compound. The rate of release of the active drug, typically, but not exclusively, by hydrolysis of the prodrug, is influenced by several factors, but especially by the type of bond joining the active drug to the modifier. Care must be taken to avoid preparing prodrugs which are eliminated through the kidney or reticular endothelial system, etc., before a sufficient amount of the parent compound is released. By incorporating a polymer as part of the prodrug system, one can increase the circulating half-life of the drug. However, in some situations, such as with alkaloids, it has been determined that when only one or two polymers of less than about 10,000 daltons are conjugated thereto, the resulting conjugates are rapidly eliminated in vivo especially if a somewhat hydrolysis-resistant linkage is used. In fact, such conjugates are so rapidly cleared from the body that even if a hydrolysis-prone ester linkage is used, not enough of the parent molecule is regenerated in vivo. This is often not a concern with moieties such as proteins, enzymes and the like, even when hydrolysis-resistant linkages are used. In those cases multiple polymer strands, each having a molecular weight of about 2–5 kDa, are used to further increase the molecular weight and circulating half-life.

One way in which these problems have been addressed is described, for example, by co-owned patent applications Ser. Nos. 09/183,557, filed Oct. 30, 1998, now U.S. Pat. No. 6,180,095 and 08/992,435, filed on Dec. 17, 1997, now abandoned. These teach double prodrugs, i.e., tripartate, that comprise polymer conjugates of various biologically-effective materials, and methods of making these conjugates. The double prodrug linkages are selected to hydrolyze in vivo at a rate which generates sufficient amounts of the "second" and more reactive prodrug compound within a suitable time after administration by, e.g., a 1,4-aryl or 1,6-aryl (e.g, benzyl) elimination reaction, providing improved control of the pharmacokinetics of a number of small molecule drugs, agents and the like. However, further opportunities for particularly selective targeting of diagnostic and/or therapeutic agents to tissues or cells of interest, by means of a rationally designed prodrug conjugate remain.

One particularly desirable target tissue for prodrugs is tumor tissue. It is well known that tumors generally exhibit abnormal vascular permeability characterized by enhanced permeability and retention ("EPR effect"). This EPR effect advantageously allows biologically-effective materials, in the form of macromolecules, e.g., protein(s) such as enzymes and/or antibodies and derivatives or fragments thereof, or the like, to readily enter tumor interstitial tissue space (see, for example, the review article by Maeda et al., 2000, *J. of Controlled Release*, 65:271–284, incorporated by reference herein). Certain other tissues, in addition to tumors, can exhibit this same EPR effect, under conditions of inflammation, and the like.

In brief, and without being bound by any theory or hypothesis as to the working of the EPR effect, it is believed that the EPR effect allows penetration of large molecule or macromolecule substances, including polymer-based delivery systems. This provides a substantially selective delivery of polymer conjugates into tumor tissue space, e.g., tumor interstitial space. Thereafter, however, the same EPR effect is believed to allow the released prodrug(s) and/or any newly released relatively low molecular weight, biologically-effective materials, to rapidly diffuse out of the extracellular tissue space of the targeted tissue. It is believed that if the released active agent fails to be taken up by the surrounding cells at a sufficient rate, they diffuse away from the release site in the ongoing blood or lymphatic flow.

Thus, there continues to be a need to provide additional technologies for forming prodrugs which would benefit from the multiple level prodrug concept and compensate or control for the EPR effect by allowing for more rapid update or transport of the released biologically-effective materials into tumor cells and/or cells of other tissues of interest that exhibit the EPR effect.

SUMMARY OF THE INVENTION

Broadly, the invention provides for a tetrapartate prodrug in the form of a compound of Formula I:

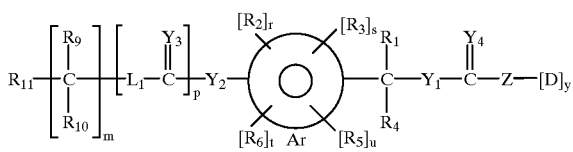

(I)

wherein:

$L_1$ is a bifunctional linking moiety.

Broadly, D is a moiety that is a leaving group, or a residue of a compound to be delivered into a cell. More particularly, D is a residue of an active biological material, or H and (y) is a positive integer equal to 1 or greater. Preferably, (y) ranges from 1 to about 5. When (y) is greater than 1, each D moiety is independently selected.

D can be any biologically active material that it is desired to deliver into a target cell or cells of an animal in need of such treatment, including anti-inflammatory agents, detoxifying agents, anticancer agents, and diagnostics for any of these or other conditions.

Preferably, D is an anticancer agent, an anticancer prodrug, a detectable tag, and combinations thereof. Any anticancer agent or suitable tag that can be linked to the tetrapartate prodrug is contemplated. Simply by way of example, these include an anthracycline compound, a topoisomerase I inhibitor, daunorubicin, doxorubicin; p-aminoaniline to name but a few.

When D is a leaving group, D can be, e.g., N-hydroxybenzotriazolyl, halogen, N-hydroxyphthalimidyl, p-nitrophenoxy, imidazolyl, N-hydroxysuccinimidyl and/or thiazolidinyl thione.

Z is covalently linked to $[D]_y$, wherein Z is a moiety that is actively transported into a target cell, a hydrophobic moiety, and combinations thereof. Optionally, Z is monovalent, multivalent, or more preferably, bivalent, wherein (y) is 1 or 2. Z itself optionally includes an amino acid residue, a sugar residue, a fatty acid residue, a peptide residue, a $C_{6-18}$ alkyl, a substituted aryl, a heteroaryl, —C(=O), —C(=S), and —C(=$NR_{16}$), where are $R_{16}$ is as defined below.

When Z includes at least one amino acid residue, the amino acid is, e.g., alanine, valine, leucine, isoleucine, glycine, serine, threonine, methionine, cysteine, phenylalanine, tyrosine, tryptophan, aspartic acid, glutamic acid, lysine, arginine, histidine, proline, and/or a combination thereof, to name but a few. When Z includes a peptide, the peptide ranges in size, for instance, from about 2 to about 10 amino acid residues. In one preferred embodiment, the peptide is Gly-Phe-Leu-Gly (SEQ ID NO: 1) or Gly-Phe-Leu.

In addition, $Y_1$ through $Y_4$ are independently O, S, or $NR_{12}$; and $R_{11}$ is a mono- or divalent polymer residue.

$R_1$, $R_4$, $R_9$, $R_{10}$, $R_{12}$ and $R_{16}$ are independently hydrogen, $C_{1-6}$ alkyl, $C_{3-12}$ branched alkyl, $C_{3-8}$ cycloalkyl, $C_{1-6}$ substituted alkyl, $C_{3-8}$ substituted cycloalkyl, aryl, substituted aryl, aralkyl, $C_{1-6}$ heteroalkyl, and/or substituted $C_{1-6}$ heteroalkyl.

$R_2$, $R_3$, $R_5$ and $R_6$ are independently hydrogen, $C_{1-6}$ alkyl, $C_{1-6}$ alkoxy, phenoxy, $C_{1-8}$ heteroalkyl, $C_{1-8}$ heteroalkoxy, substituted $C_{1-6}$ alkyl, $C_{3-8}$ cycloalkyl, $C_{3-8}$ substituted cycloalkyl, aryl, substituted aryl, aralkyls, halo-, nitro- and cyano-, carboxy-, $C_{1-6}$ carboxyalkyl and/or substituted $C_{1-6}$ alkylcarbonyl.

Ar is a moiety which, when included in Formula (I), forms a multi-substituted aromatic hydrocarbon or a multi-substituted heterocyclic group; wherein (m), (r), (s), (t), and (u) are independently zero or one, (p) is zero or a positive integer. In certain preferred embodiments, (p) is 1.

$L_1$ is independently one of the following:

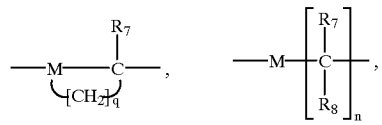

-continued

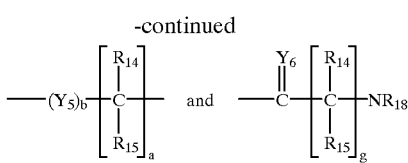

wherein:

M is X or Q; where X is an electron withdrawing group;
Q is a moiety containing a free electron pair positioned three to six atoms from

Simply by way of example, Q is one of the following: $C_{2-4}$ alkyls, cycloalkyls, aryls, and aralkyl groups substituted with a member of the group consisting of NH, O, S, —$CH_2$—C(O)—N(H)—, and/or ortho-substituted phenyls;
X is, for instance any one of O, $NR_{20}$,

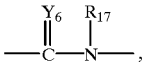

S, SO and $SO_2$;
(a) and (n) are independently zero or a positive integer; (b) is zero or one; (g) is a positive integer of 1 or greater;
(q) is three or four;
$R_7$, $R_8$, $R_{14}$, $R_{15}$, $R_{17}$, $R_{18}$ and $R_{20}$ are independently selected from the same group as that which defines $R_1$; and $Y_5$ and $Y_6$ are independently O, S, or $NR_{12}$. It will be appreciated that when (y) is greater than 1, each of the D moieties are the same or different, respectively.

Preferably, (g) ranges from 1 to about 20, or more, but more typically ranges from 1 to about 10.

Optionally,

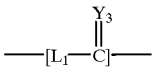

comprises an amino acid residue, either naturally occurring or non-naturally occurring.

$R_{11}$ is a mono- or bivalent polymer, e.g., having a number average molecular weight of from about 2,000 to about 100,000 daltons.

Methods of preparing the tetrapartate prodrugs of the invention are also provided. In one embodiment, the method includes reacting a compound of formula (III):

(III)

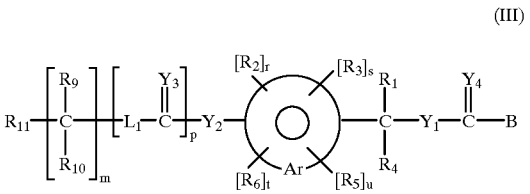

with a compound of the formula (IV):

Lx—Z—$[D]_y$;   (IV)

wherein B is a leaving group for Formula (III) and is defined as above for when D is a leaving group.

Lx is a leaving group for Formula (IV) and is defined as above for when D is a leaving group.

$L_1$, Ar, Z, D, $R_1$–$R_6$, $R_9$–$R_{11}$, $Y_1$–$Y_3$, and integers are defined as above. The reaction between (III) and (IV) is preferably conducted in the presence of a solvent and a base. The solvent is, for example, chloroform, methylene chloride, toluene, dimethylformamide and/or combinations thereof Dimethylformamide is generally preferred. The base is, for example, dimethylaminopyridine, diisopropylethylamine, pyridine, triethylamine and/or combinations thereof.

Yet another method of preparing a tetrapartate prodrug of the invention is conducted by reacting a compound of formula (V)

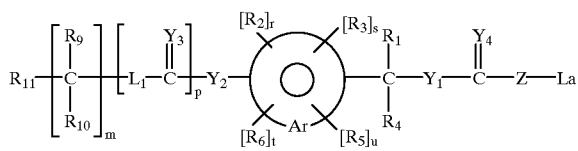

(V)

with a biologically active material; wherein

La is a leaving group as defined when D is a leaving group, $L_1$, Ar, Z, D, $R_1$–$R_6$, $R_9$–$R_{11}$, $Y_1$–$Y_3$, and integers are defined as above.

The reaction between (V) and the biologically active material is conducted in the presence of a coupling agent, e.g., 1,3-diisopropylcarbodiimide, a dialkyl carbodiimides, 2-halo-1-alkyl-pyridinium halide, 1-(3-dimethylamino-propyl)-3-ethyl carbodiimide, 1-propanephosphonic acid cyclic anhydride, phenyl dichlorophosphates, and/or combinations thereof. The reaction between (V) and the biologically active material is conducted in the presence of a solvent and a base, e.g., as described above for the previous synthetic method.

Methods of using the inventive tetrapartate prodrugs are also provided, e.g., by treating a disease or disorder in an animal, by administering a pharmaceutically acceptable composition comprising an effective amount of a compound of Formula I, to an animal in need thereof. In particular, a method is provided of delivering a biologically active material D, into a cell in need of treatment therewith, by a process of:

administering a compound of Formula I to an animal wherein the cell is present, and wherein Formula I is hydrolyzed in vivo extracellularly to yield:

Formula I-(i)

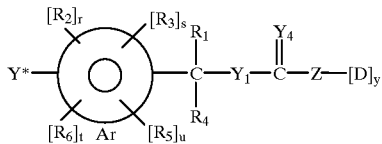

wherein $Y^*$ is the remainder of $Y_2$, and is independently selected from the group consisting of HO—, HS—, or $HNR_{12}$—;

and Formula I-(i) then spontaneously hydrolyzes to

Format I-(ii)

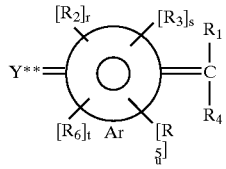

and $CO_2$, and Formula I-(iii) Z—$[D]_y$;

wherein $Y^{**}$ is the remainder of $Y^*$, and is independently selected from the group consisting of O, S, or $NR_{12}$ and Z—$[D]_y$ crosses the membrane of the cell, and is hydrolyzed therein to release D.

DETAILED DESCRIPTION OF THE INVENTION

Figure 1:
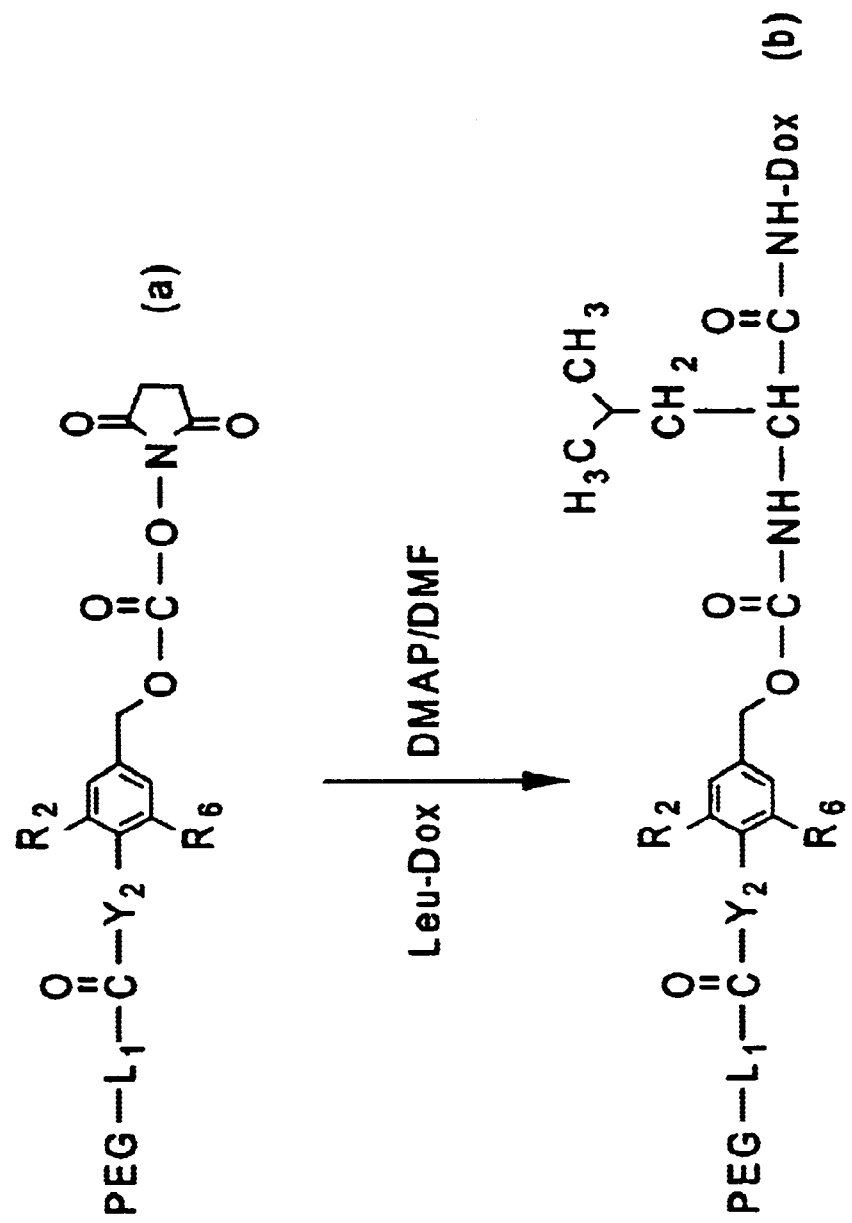
FIG. 1: Illustrates a summary of the reaction scheme for the preparation of the tetrapartate prodrugs of doxorubicin by the methods of Examples 1–5, wherein the aromatic is a benzyl derivative.

Accordingly, the invention provides triple prodrugs compositions, hereinafter, "tetrapartate" prodrugs for delivering a biologically active material into certain important target cells, such as, for instance, tumor cells, as well as methods of making and using the same. The tetrapartate prodrug compositions of the present invention contain hydrolyzable linkages between the polymer portion and a biologically active material. The biologically active material is, for example, a moiety derived from a biologically active nucleophile, i.e., a native or unmodified drug or diagnostic tag. These linkages are preferably ester and/or amide linkages designed to hydrolyze at a rate which generates sufficient amounts of the biologically active parent compound in a suitable time. The term "sufficient amounts" for purposes of the present invention shall mean an amount which achieves a therapeutic effect.

The present invention is broadly based upon the principle that biologically active materials suitable for incorporation into the polymer-based prodrug conjugates, e.g., the double prodrug compositions as discussed supra, may themselves be substances/compounds which are not active after hydrolytic release from the linked composition, but which will become active after undergoing a further chemical process/reaction, thus providing triple-acting prodrugs. These triple acting prodrugs are referred to herein as "tetrapartate" prodrugs because the inventive conjugates are provided in essentially four parts.

With the tetrapartate prodrugs of the invention, a therapeutic or diagnostic agent that is delivered to the bloodstream by the above-described double prodrug transport system) will remain inactive until entering or being actively transported into a target cell of interest, whereupon it is activated by intracellular chemistry, e.g., by an enzyme or enzyme system present in that tissue or cell.

In particular, it has now been discovered that when certain types of additional moieties are linked to the biologically active material as part of the above described double prodrug conjugates, the effectiveness of many such biologically active materials is markedly increased, relative to the effectiveness seen with analogous prodrugs that lack such additional moiety. The tetrapartate prodrug conjugates of the invention are thought to provide enhanced effectiveness, e.g., for therapeutic and/or diagnostic activity, in the delivery and activity of certain biologically active materials, e.g., particularly small molecule therapeutic and diagnostic agents. The tetrapartate prodrugs of the invention prepared so that in vivo hydrolysis of the polymer-based conjugate cleaves the conjugate so as to release the active biological material into extracellular fluid, while still linked to the additional moiety. The biologically active materials are preferably, but not exclusively, small molecule therapeutic and/or diagnostic agents. As exemplified below, in one preferred embodiment these are small molecule anticancer agents, and the tissue to be treated is tumor tissue.

Without intending to be bound by any theory or hypothesis as to how the invention might operate, it is believed that, depending upon the additional moiety selected as a transport enhancer, the rate of transport of a biologically active material into tumor cells is by the delivery of a biologically active material into extracellular tissue space, e.g., of a tissue exhibiting an EPR effect, in a protected and/or transport-enhanced form. For convenience in description, the "additional moiety(s)" as mentioned are described herein as, "transport enhancers."

However, in providing this convenient descriptive term, it is not intended to limit the scope of the invention solely to added moieties that solely enhance transport of biologically active materials into targeted cells, since it is believed that additional or alternative mechanisms, such as protection of the Z—[D]$_y$ from extracellular hydrolytic enzyme activity, may contribute to the advantages of the inventive tetrapartate prodrug.

In a further still option, the transport enhancer is selected from among known substrates for a cell membrane transport system. Simply by way of example, cells are known to actively transport certain nutrients and endocrine factors, and the like, and such nutrients, or analogs thereof, are readily employed to enhance active transport of a biologically effective material into target cells. Examples of these nutrients include amino acid residues, peptides, e.g., short peptides ranging in size from about 2 to about 10 residues or more, simple sugars and fatty acids, endocrine factors, and the like.

Desirable amino acid residues include all of the known naturally-occurring L-amino acids. For example, L-isoleucine as a transport enhancer is exemplified in the Examples provided below. Surprisingly, it has also been discovered that D-amino acids are useful as transport enhancers, e.g., both D and L-alanine, and other analogous amino acid optical isomers, show the same activity. Derivatives and analogs of the naturally occurring amino acids, as well as various art-known non-naturally occurring amino acids (D or L), hydrophobic or non-hydrophobic, are also contemplated to be within the scope of the invention. Simply by way of example, amino acid analogs and derivates include: 2-aminoadipic acid, 3-aminoadipic acid, beta-alanine, beta-aminopropionic acid, 2-aminobutyric acid, 4-aminobutyric acid, piperidinic acid, 6-aminocaproic acid, 2-aminoheptanoic acid, 2-aminoisobutyric acid, 3-aminoisobutyric acid, 2-aminopimelic acid, 2,4-diaminobutyric acid, desmosine, 2,2-diaminopimelic acid, 2,3-diaminopropionic acid, n-ethylglycine, N-ethylasparagine, 3-hydroxyproline, 4-hydroxyproline, isodesmosine, allo-isoleucine, N-methylglycine, sarcosine, N-methylisoleucine, 6-N-methyllysine, N-methylvaline, norvaline, norleucine, ornithine, and others too numerous to mention, that are listed in 63 *Fed. Reg.*, 29620, 29622, incorporated by reference herein.

Short peptides are, for example, peptides ranging from 2 to about 10, or more, amino acid residues, as mentioned supra. In this embodiment of the invention, it is believed that such peptide transport enhancers need not be hydrophobic, but are thought to function in other ways to enhance uptake and/or to protect the linked small molecule agents from premature hydrolysis in the general bloodstream. For instance, peptide transport enhancers, and other transport enhancers of similar molecular weight ranges, are thought to sterically hinder cleavage from the biologically active agent by plasma-based hydrolytic enzymes, but are then cleaved within a target cell by various peptides and/or proteases, such as cathepsins.

Preferably, the transport enhancer is a hydrophobic moiety. Without meaning to be bound to any theory or hypothesis as to how hydrophobicity contributes to efficacy, it is believed that a hydrophobic moiety inhibits the extracellular cleavage of the transport enhancer away from the active biological agent, by inhibiting the attack of hydrolytic enzymes, etc. present in the extracellular tissue space, e.g., in the plasma. Thus, preferred transport enhancers include, e.g., hydrophobic amino acids such as alanine, valine, leucine, isoleucine, methionine, proline, phenylalanine, tyrosine, and tryptophane, as well as non-naturally occurring derivatives and analogs thereof, as mentioned supra.

In a further option, the transport enhancer is a hydrophobic organic moiety. Simply by way of example, the organic moiety is a $C_{6-18}$, or larger, alkyl, aryl or heteroaryl-substituted or nonsubstituted. The organic moiety transport enhancer is also contemplated to encompass and include organic functional groups including, e.g., —C(=S) and/or —C(=$Y_3$).

In order to appreciate the nature of the invention, several definitions and explanations are provided as follows. The term, "tetrapartate" refers to prodrug conjugates, and in particular, to conjugates incorporating the features of the double prodrugs, as discussed supra, and an additional moiety serving as a transport enhancer positioned between the residue of the biologically active compound and the polymer moiety to form a 4-part structure wherein the biologically active agent is the fourth part of the conjugate. This structure provides that the residue of the biologically active compound is optimized for transport and release substantially into a target cell. The fourth element of the "tetrapartate" is therefore the residue of the biologically active compound, itself. Further, diagnostic tetrapartate conjugates incorporating detectable tags are also contemplated, and the use of the terms, "tetrapartate prodrug," or simply, "prodrug" herein, with reference to the inventive conjugates, broadly also includes conjugates and methods of making and delivering diagnostic reagents, including tagged drugs, as well, unless otherwise specified or distinguished.

For purposes of the present invention, the terms, "biologically active material," and "biologically active compound," and/or "biologically active agent," etc., are used interchangeably unless otherwise stated. These terms refer, for example, to a drug or pharmaceutical, and/or a diagnostic agent or reagent, such as a detectable label or marker. The terms "drug," "agent," "medicinal agent," and "active agent" herein refer to compound(s) with useful activity, particularly when administered to an animal, in vivo, and/or to precursors of the same, unless otherwise stated.

As noted in the previous lines, biological activity is any property of such a material or compound that is useful in an animal or person, e.g., for medical, and/or diagnostic purposes. Preferably, the biological activity is manifested in an intracellular space, i.e., the drug or diagnostic agent preferably but not exclusively is useful once delivered/released into the cytoplasm and/or nucleus of one or more types of target cell of interest.

For purposes of the present invention, the use of the singular or plural is not meant to be limiting of the numerical number of the referenced item or object. Thus, the use of the singular to refer to a cell, polymer or drug does not imply that only one cell is treated, only one molecule is prepared or employed, and/or only one drug is employed, and the use of the plural does not exclude application to a single referenced item, unless expressly stated. Further to this point, for purposes of the present invention, the terms, "cell," "cell type," "target cell," and etc., are used interchangeably unless otherwise specified and refer to both singular and plural cells, however organized into a tissue, tissues or other system or component, normal or pathological, of an animal or patient to be treated.

For purposes of the present invention, the term "residue" shall be understood to mean that portion of a biologically active compound which remains after it has undergone a reaction in which the prodrug carrier portion has been attached by modification of e.g., an available hydroxyl or amino group, to form, for example, an ester or amide group, respectively.

For purposes of the present invention, the term "alkyl" shall be understood to include, e.g., straight, branched, substituted $C_{1-12}$ alkyls, including alkoxy, $C_{3-8}$ cycloalkyls or substituted cycloalkyls, etc.

When the prodrugs of the present invention include the double prodrugs taught by co-owned Ser. Nos. 09/183,557 now U.S Pat. No. 6,180,095 and Ser. No. 08/992,435, now abandoned it is generally preferred that the polymeric portion is first released by hydrolysis and then the resultant "second prodrug" moiety undergoes a 1,4- or 1,6-aryl (e.g., benzyl) elimination reaction to regenerate, for example, a moiety comprising a further prodrug, Thereafter, the released moiety diffuses and/or is transported into target cells, where a substantial proportion of the incorporated remainder of the prodrug is further cleaved or hydrolyzed by intracellular enzymes to release the biologically active compound.

In addition, the terms "cancer" or "tumor" are clinically descriptive terms which encompass a myriad of diseases characterized by cells that exhibit unchecked and abnormal cellular proliferation. The term "tumor", when applied to tissue, generally refers to any abnormal tissue growth, i.e., excessive and abnormal cellular proliferation. The term "cancer" is an older term which is generally used to describe a malignant tumor or the disease state arising therefrom. Alternatively, the art refers to an abnormal growth as a neoplasm, and to a malignant abnormal growth as a malignant neoplasm. These general clinical terms, when used with reference to cells, tissues, and/or one or more conditions characterized as a disease or disorder, as used herein, are intended to be interchangeable and synonymous, unless otherwise specified.

Broadly, the compounds according to the invention are as follows.

A. Formula (I)

In one aspect of the invention, there are provided compounds of formula (I):

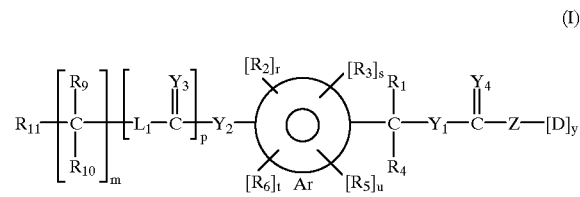

(I)

wherein:

$L_1$ is a bifunctional linking moiety; for example, $L_1$ is independently one of the following:

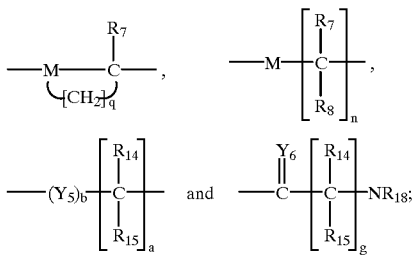

Simply by way of example, in one optional embodiment, $L_1$ is

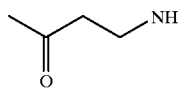

In a further embodiment, Z is a transport enhancer and/or protector that is covalently linked to D, wherein Z is selected to enhance or improve intracellular delivery of Z—[D]$_y$ into a cell; relative to the intracellular delivery of D without Z.

In certain embodiments, Z optionally includes one of the following: an amino acid residue, a sugar residue, a fatty acid residue, a peptide residue, a $C_{6-18}$ alkyl, a substituted aryl, a heteroaryl, —C(=O), —C(=S), and —C(=NR$_{16}$), and/or combinations thereof.

D is a moiety that is a leaving group, or a residue of a compound to be delivered into a cell. Preferably but not exclusively, D is an active biological material, or H.

The artisan will appreciate that each D can be selected independently, so that there can be as many as five, or more, different types of moieties linked to Z for delivery into a target cell of interest. Preferably, D is a therapeutic agent or drug, but D is also optionally a diagnostic agent.

Simply by way of illustration, and in certain additional optional embodiments, y is 2 and Z is divalent, D can be two moieties, including both a therapeutic agent and a diagnostic tag for delivery into the same cell type or into the cells of a tissue type of interest. Further still, such plural D moieties will comprise multiple different therapeutic agents, preferably targeted to a single type of cell, where when delivered and released together, the different agents act synergistically to achieve a desired therapeutic effect. In one preferred optional embodiment, D is one or more anticancer agent(s) and/or an anticancer prodrug, or residue thereof.

In certain further embodiments, D is

H, or

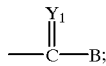

where

B is H, a leaving group, a residue of an amine-containing moiety, or a residue of a hydroxyl-containing moiety;

$Y_{1-6}$ are independently O, S or NR$_{12}$;

M is X or Q; where

X is an electron withdrawing group;

Q is a moiety containing a free electron pair positioned three to six atoms from

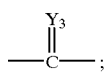

$R_1$, $R_4$, $R_7$, $R_8$, $R_9$, $R_{10}$, $R_{12}$, $R_{14}$, $R_{15}$, $R_{16}$ and $R_{18}$ are independently selected from the group consisting of hydrogen, $C_{1-6}$ alkyls, $C_{3-12}$ branched alkyls, $C_{3-8}$ cycloalkyls, $C_{1-6}$ substituted alkyls, $C_{3-8}$ substituted cycloalkyls, aryls, substituted aryls, aralkyls, $C_{1-6}$ heteroalkyls and substituted $C_{1-6}$ heteroalkyls;

$R_2$, $R_3$, $R_5$ and $R_6$ are independently selected from the group consisting of hydrogen, $C_{1-6}$ alkyls, $C_{1-6}$ alkoxys, phenoxy, $C_{1-8}$ heteroalkyls, $C_{1-8}$ heteroalkoxy, substituted $C_{1-6}$ alkyls, $C_{3-8}$ cycloalkyls, $C_{3-8}$ substituted cycloalkyls, aryls, substituted aryls, aralkyls, halo-, nitro- and cyano-, carboxy-, $C_{1-6}$ carboxyalkyls and $C_{1-6}$ alkylcarbonyls;

Ar is a moiety which when included in Formula (I) forms a multi-substituted aromatic hydrocarbon or a multi-substituted heterocyclic group;

(b), (m), (r), (s), (t), and (u) are independently zero or one;

(a) and (n) are independently zero or a positive integer;

(p) is zero or a positive integer;

(q) is three or four; and $R_{11}$ is a polymer such as a polyalkylene oxide.

B. Description of the Ar Moiety

Referring to Formula (I), it can be seen that the Ar is a moiety, which when included in Formula (I), forms a multi-substituted aromatic hydrocarbon or a multi-substituted heterocyclic group. A key feature is that the Ar moiety is aromatic in nature. Generally, to be aromatic, the α-electrons must be shared within a "cloud" both above and below the plane of a cyclic molecule. Furthermore, the number of α electrons must satisfy the Huckle rule (4n+2). Those of ordinary skill will realize that a myriad of moieties will satisfy the aromatic requirement of the moiety and thus are suitable for use herein.

Preferred aromatic hydrocarbon moieties include, without limitation:

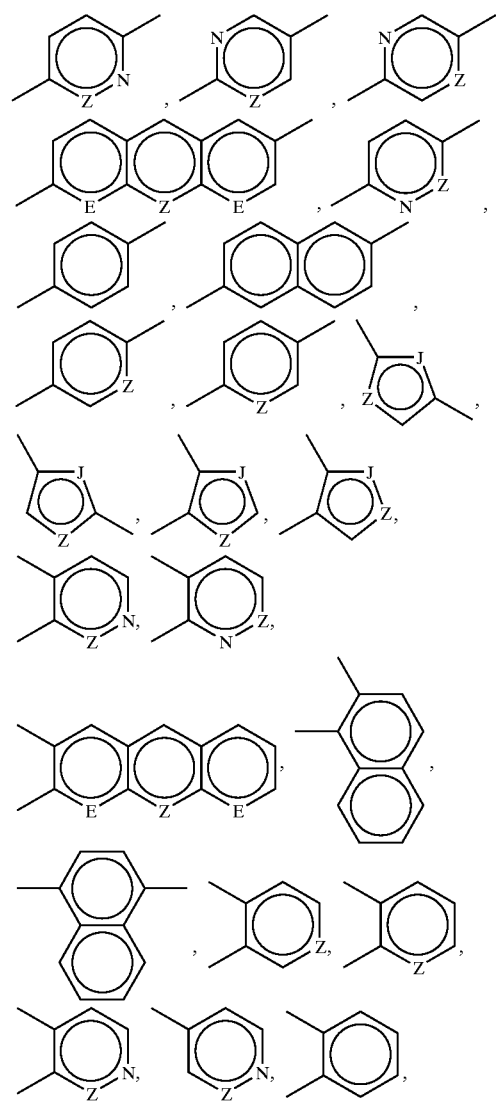

-continued

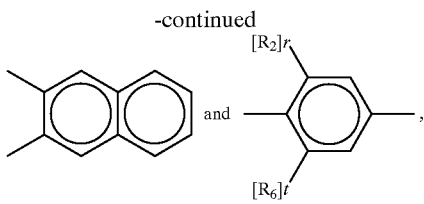

In the above-listed aromatic moieties, J is O, S, or N—$R_{19}$, E and Z are independently C—$R_{19}$ or N—$R_{19}$; and $R_{19}$ is independently selected from the same group as that which defines $R_9$ in Formula (I) e.g., hydrogen, $C_{1-6}$ alkyls, etc. Isomers of the five and six-membered rings are also contemplated as well as benzo- and dibenzo- systems and their related congeners are also contemplated. It will also be appreciated by the artisan of ordinary skill that the aromatic rings can optionally be substituted with hetero-atoms such as O, S, $NR_{13}$, etc. so long as Huckel's rule is obeyed. Furthermore, the aromatic or heterocyclic structures may optionally be substituted with halogen(s) and/or side chains as those terms are commonly understood in the art. However, all structures suitable for Ar moieties of the present invention are capable of allowing the $Y_3$ and $C(R_1)$ $(R_4)$ moieties to be in a para or an ortho arrangement with the same plane as shown in Formulas I-A and I-B, below.

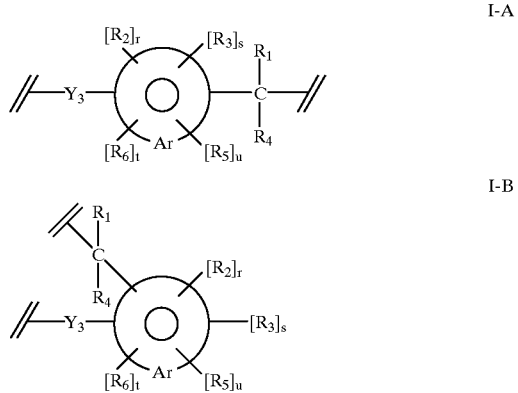

wherein all variables are as defined above for Formula (I).

When the Ar moiety includes a para arrangement of the $Y_3$ and $C(R_1)(R_4)$ moieties, preferred aspects of the present invention define (r), (s), (t), and (u) as one and $R_2$ and $R_6$ as being independently selected from the group consisting of methyl, $C_{1-6}$ alkyls, methyl, $C_{1-6}$ alkoxys, and methoxy. More preferably, $R_2$ and $R_6$ are either both methyl or methoxy moieties. Furthermore, $R_3$ and $R_5$ are preferably both hydrogen, $R_1$ and $R_4$ are preferably either hydrogen, $CH_3$ or $CH_2CH_3$. $Y_1$ through $Y_4$ (i.e., $Y_{1-4}$) are preferably O or $NR_{12}$ where $R_{12}$ is H or a $C_{1-6}$ alkyl or substituted alkyl. More preferably, $Y_1$ and $Y_4$ are O.

For purposes of the present invention, substituted alkyls include carboxyalkyls, aminoalkyls, dialkylaminos, hydroxyalkyls and mercaptoalkyls; substituted cycloalkyls include moieties such as 4-chlorocyclohexyl; aryls include moieties such as napthyl; substituted aryls include moieties such as 3-bromophenyl; aralkyls include moieties such as toluyl; heteroalkyls include moieties such as ethylthiophene; substituted heteroalkyls include moieties such as 3-methoxy-thiophene; alkoxy includes moieties such as methoxy; and phenoxy includes moieties such as 3-nitrophenoxy. Halo- shall be understood to include fluoro, chloro, iodo and bromo.

C. Linker Moiety $L_1$

As shown above, the invention includes bifunctional linking moiety $L_1$ which when combined with

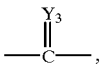

forms an amino acid residue linker, or when (p) is greater than one, a peptide residue linker.

Suitable amino acid residues can be selected from naturally-occurring or synthetic, i.e. non-naturally-occurring, amino acids including alanine, valine, leucine, isoleucine, glycine, serine, threonine, methionine, cysteine, phenylalanine, tyrosine, tryptophan, aspartic acid, glutamic acid, lysine, arginine, histidine or proline. Some preferred peptide residues include Gly-Phe-Leu-Gly (SEQ ID NO: 1) and Gly-Phe-Leu. It is noted that the terminal amino group of the amino acid or peptide residue will be proximal to $R_{11}$ (i.e. polymer). Peptides can be readily synthesized or obtained from commercial sources for inclusion herein.

In alternative embodiments, $L_1$ includes the moiety (M) which is either an electron withdrawing group (designated herein as X), or a moiety containing a free electron pair positioned three to six atoms from the

(designated herein as Q). In a particularly preferred embodiment, the tetrapartate conjugates of the invention are based upon an aromatic moiety that is a substituted benzyl, and the first two breaks in the prodrug, in vivo, are based on a 1,4 or 1,6 benzyl elimination mechanism. This embodiment provides a conjugate as illustrated by FIG. 1. In FIG. 1, an overview of the general reaction scheme followed in synthesis of the compounds produced in Examples 1–5, provided herein below, is set forth. Precursor compound (FIG. 1, compound a) is reacted in the presence of leucine doxorubicin ("leu-dox"), dimethylaminopyridine and dimethyformamide to form (FIG. 1, compound b), wherein the variables are set forth by Table 1, below.

TABLE 1

| Compound No. | Variables |
|---|---|
| 2 | $L_1$, $Y_2$ = O; $R_2$, $R_6$ = H |
| 6 | $L_1$ = NH; $Y_2$ = O; $R_2$, $R_6$ = H |
| 8 | $L_1$ = $NHCOCH_2CH_2NH$; $Y_2$ = O; $R_2$, $R_6$ = H |
| 10 | $L_1$ = $CH_2$; $Y_2$ = O; $R_2$, $R_6$ = $CH_3$ |
| 12 | $L_1$, $Y_2$ = O; $R_2$, $R_6$ = $CH_3$ |

D. The Double Prodrug Linkage Portion

The first labile bond of the tetrapartate prodrug system, which joins the $L_1$ to

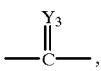

is selected to hydrolyze, such as via an esterase catalyzed hydrolysis in vivo at a rate which generates sufficient amounts of the "second" prodrug compound within a suitable time after administration. The term "sufficient amounts" for purposes of the present invention shall mean an amount which may later undergo sufficient 1,4 or 1,6-benzyl elimination in vivo to release the native compound and achieve a desired effect. Preferably, (n) is an integer from 1 to about 12. More preferably, (n) is 1 or 2.

1. The Electron Withdrawing Group X

In those aspects of Formula (I) where $L_1$ includes M, the moiety may be an electron withdrawing group, designated herein as X. For purposes of the present invention, "electron withdrawing groups" are groups which tend to pull shared electrons toward themselves thereby making carbon more electro-positive. This, in turn, destabilizes the carbonyl moiety, causing more rapid hydrolysis. Thus, when X is in the α position to the ester, it modulates the rates of hydrolysis and enzymatic cleavage. In particular, X can be moieties such as O, $NR_{20}$,

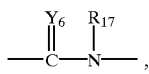

S, SO and $SO_2$ where $Y_6$ is the same as that defined by $Y_1$, $R_{12}$ and $R_{17}$ are the same as defined above i.e., H, $C_{1-6}$ alkyls, branched alkyls, aryls, etc. $R_1$ is the same as defined by Formula I, supra. Preferably, however, when X is $NR_{20}$, $R_{20}$ is H, a $C_{1-6}$ alkyl such as methyl or ethyl or substituted $C_{1-6}$ alkyl. It is preferred that X is either O or $NR_{20}$.

2. Q Portion of $L_1$

Alternatively, when $L_1$ includes Q, which is a moiety containing a free electron pair positioned three to six atoms from the

moiety, the polymer, $R_{11}$, is preferably attached to Q via a heteroatom such as oxygen. In a preferred embodiment, the free electron pair is five atoms from this oxygen. Q can be selected from the non-limiting list of $C_{2-4}$ alkyls or cycloalkyls, aryls or aralkyl groups substituted with a member of the group consisting of O, S and $NR_{12}$. The free electron pair can be anywhere along the Q moiety as long as the defined spacing between the free electron pair and $Y_4$ is maintained.

In these embodiments, $R_{11}$ is attached to Q via $NR_{12}$, O, or S. Thus, Q assists hydrolysis of the prodrug linkage by anchimeric assistance because the free electron pair moiety can generate a three- to six-membered, but preferably five-membered, ring by-product upon hydrolysis of the preferably ester linkage.

Q can also be selected from the group consisting of $C_{2-4}$ alkyls, cycloalkyls, aryls, aralkyl groups substituted with a member of the group consisting of NH, O, S, —$CH_2$—C(O)—N(H)—, and ortho-substituted phenyls such as

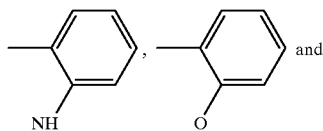

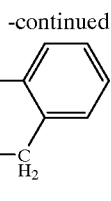

wherein $R_{21}$ is selected from the same group as that which defines $R_{12}$ supra and T is any moiety linked to Q.

3. Drug Generation Via Hydrolysis of the Prodrug

The prodrug compounds of the present invention are designed so that the $t_{1/2}$ of hydrolysis is less than the $t_{1/2}$ of elimination in plasma. The linkages included in the compounds have in-vivo hydrolysis rates, in plasma, that are short enough to allow sufficient amounts of the transport enhanced conjugate with parent compounds, i.e., the amino- or hydroxyl-containing biologically active compound, to be released prior to elimination. Some preferred compounds of the present invention, i.e., those in which (n) is 1, have a $t_{1/2}$ for hydrolysis in plasma ranging from about 5 minutes to about 12 hours. Preferably, the compositions have a plasma $t_{1/2}$ of hydrolysis ranging from about 0.5 to about 8 hours and most preferably from about 1 to about 6 hours.

4. 1,4 or 1,6-Benzyl Elimination; Release of Native Drug-Linked to Uptake Enhancer and Intracellular Release of Native Drug from Transport Enhancer Once the hydrolysis of the double prodrug portion of the conjugate has taken the place in vivo, usually via esterase activity or pH moderated activity or cyclization reaction, the polymeric residue is cleaved and the resultant second prodrug moiety remains. Without meaning to be bound by any theory or hypothesis as to how the tetrapartate conjugates or prodrugs of the invention operate, it is believed that once the biologically effective material as linked to the uptake, enters a target cell, various intracellular peptidases and/or proteases, including e.g., cathepsins, cleave, e.g., by enzymatic hydrolysis, the transport enhancer moiety to release the biologically effective material within the target cell. The following degradation scheme is provided for illustrative purposes and is not intended to limit the scope of the invention.

Figure 2A:
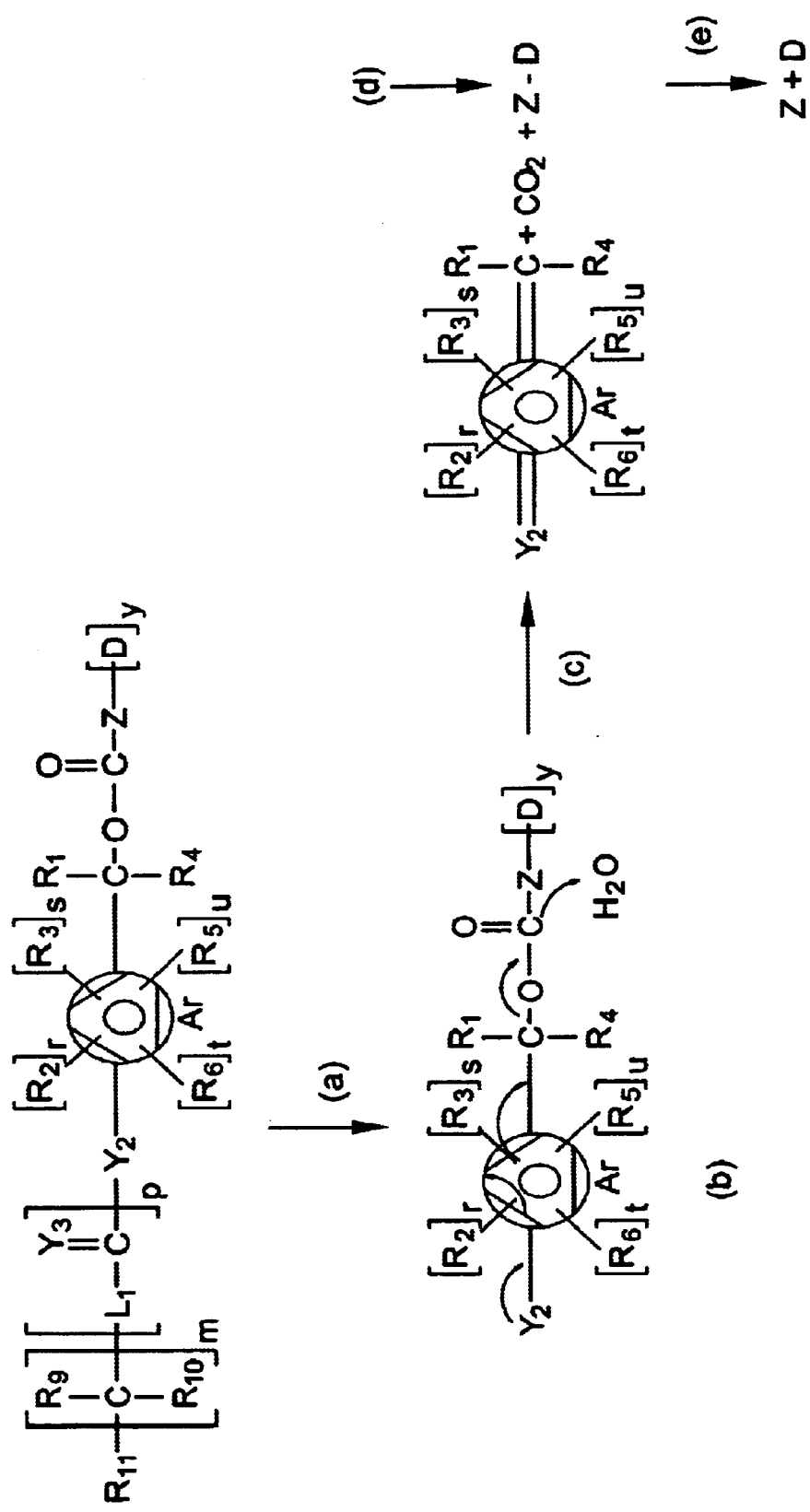
FIG. 2A: Illustrates a general reaction scheme for the degradation of the tetrapartate prodrug prodrug by sequential hydrolysis of the compound of Formula I. Thus, variables of FIG. 1 are defined as for Formula I, supra. Symbols for reaction steps: (a): controllable rate in vivo cleavage; (b) "first" prodrug; (c) fast reaction in presence of water; (d) Z—D is the "second" prodrug and it is released substantially into extracellular space; (e) uptake of Z—D into cells and intracellular enzymatic hydrolysis releases D.
Figure 2B:
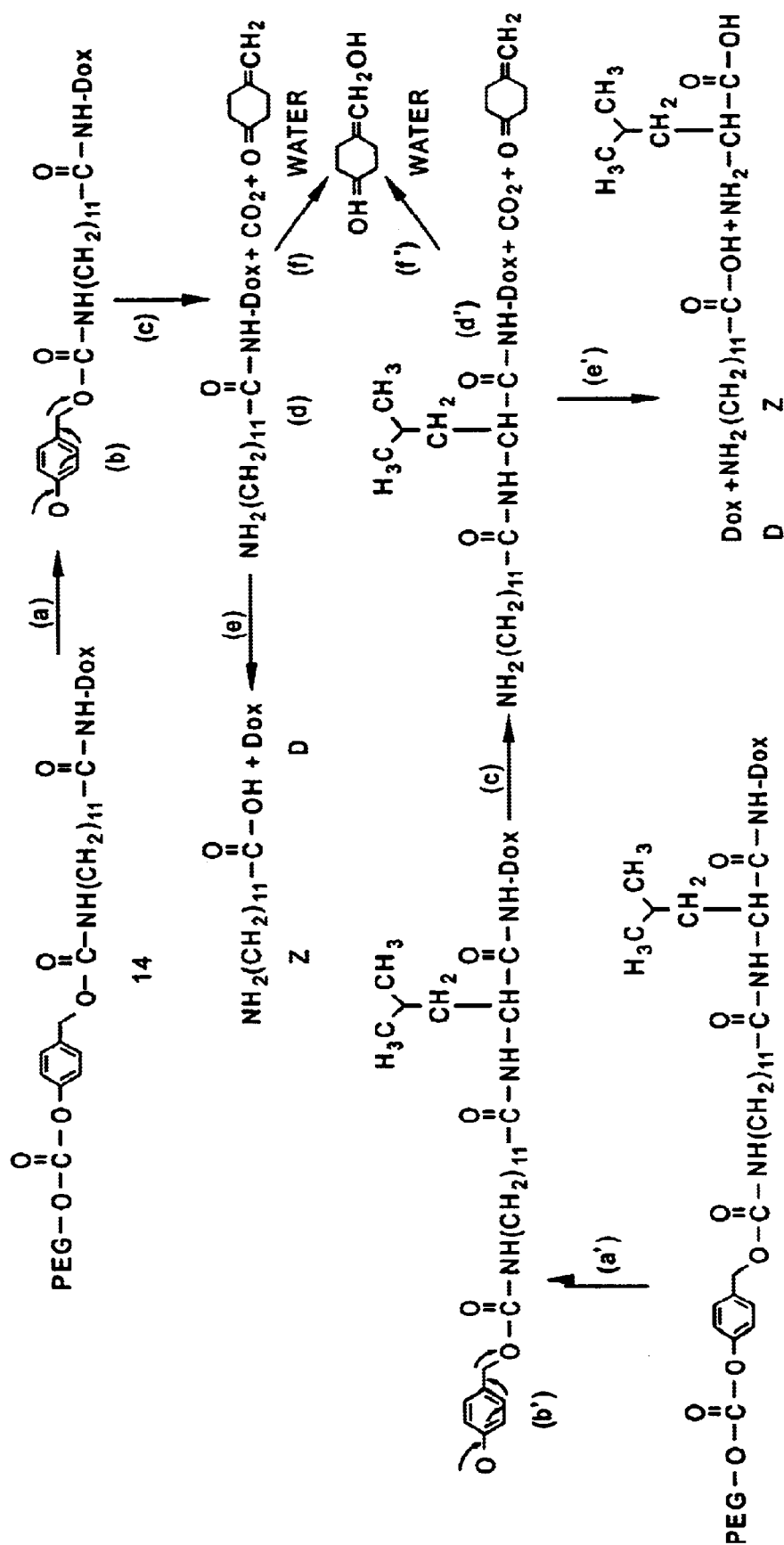
FIG. 2B: Illustrates a specific reaction schemes for the degradation of tetrapartate prodrug compound identified herein as compounds 14 (top scheme) and 17 (bottom scheme) wherein both schemes result in a final product of doxorubicin substantially released within a cell. Symbols for reaction steps are analogous to those of FIG. 2A, so that (a), (b), (c), (d) and (e) are the analogous reaction steps for the in vivo degradation of compound 14, and that (a'), (b'), (c'), (d') and (e') are the analogous reaction steps for the in vivo degradation of compound 17. The products of step (e') are D and Z, but the figure illustrates that much of Z further degrades into a $C_{12}$ acid and leucine.
Figure 3:
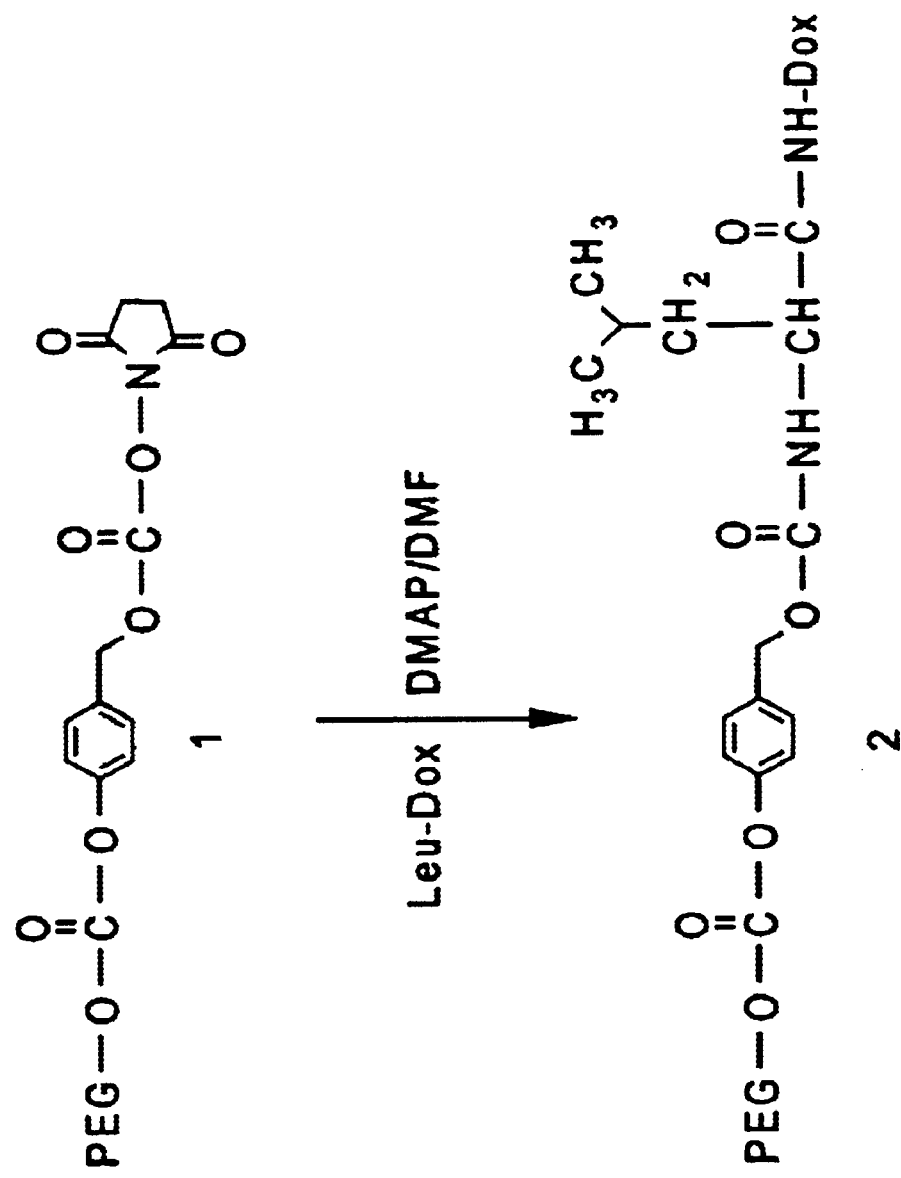
FIG. 3: Illustrates a schematic of the synthesis of compound 2 as described by Method 1 of Example 1.
Figure 4:
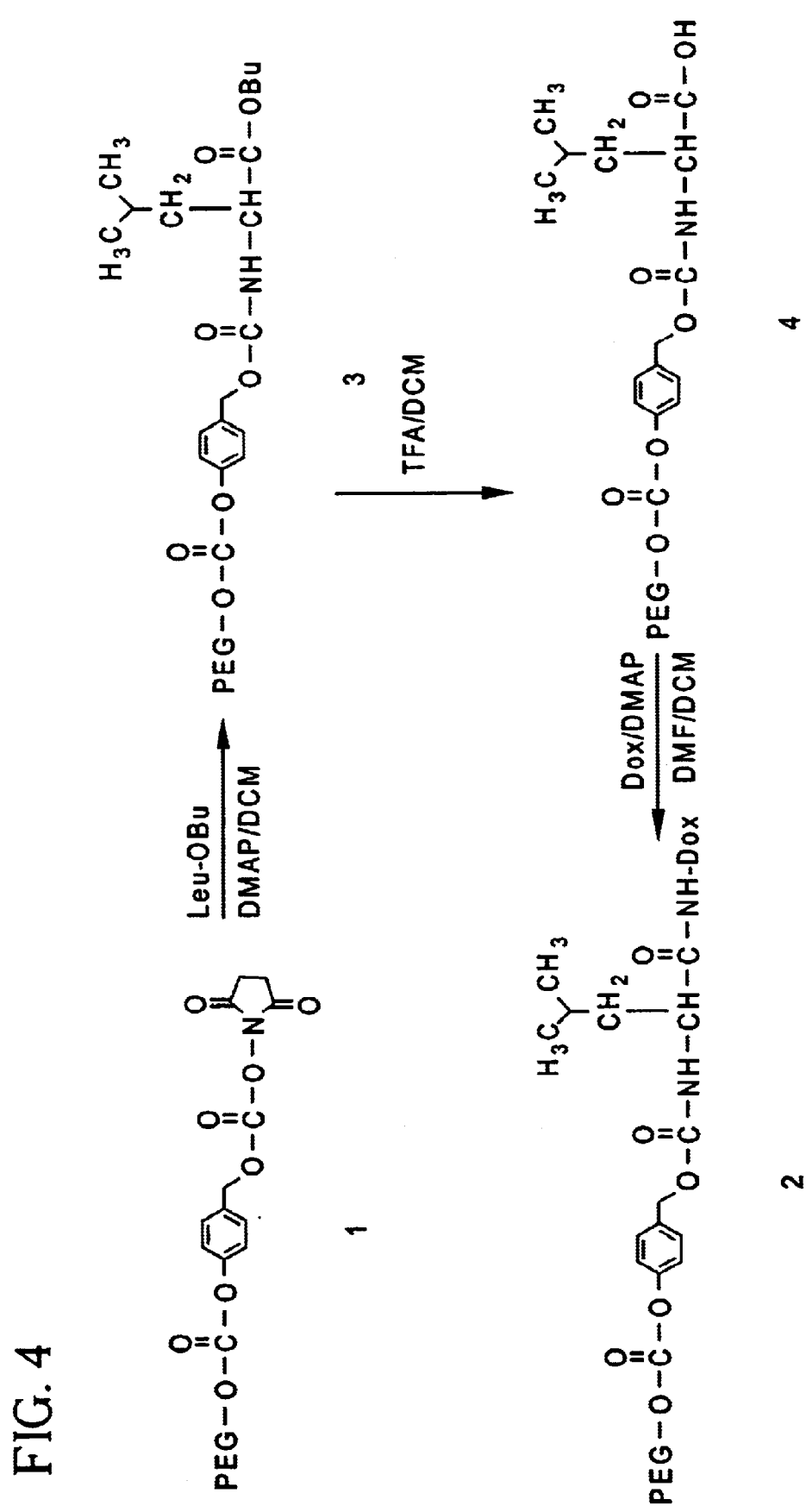
FIG. 4: Illustrates the synthesis of compound 2, as described by Method 2 of Example 1.
Figure 5:
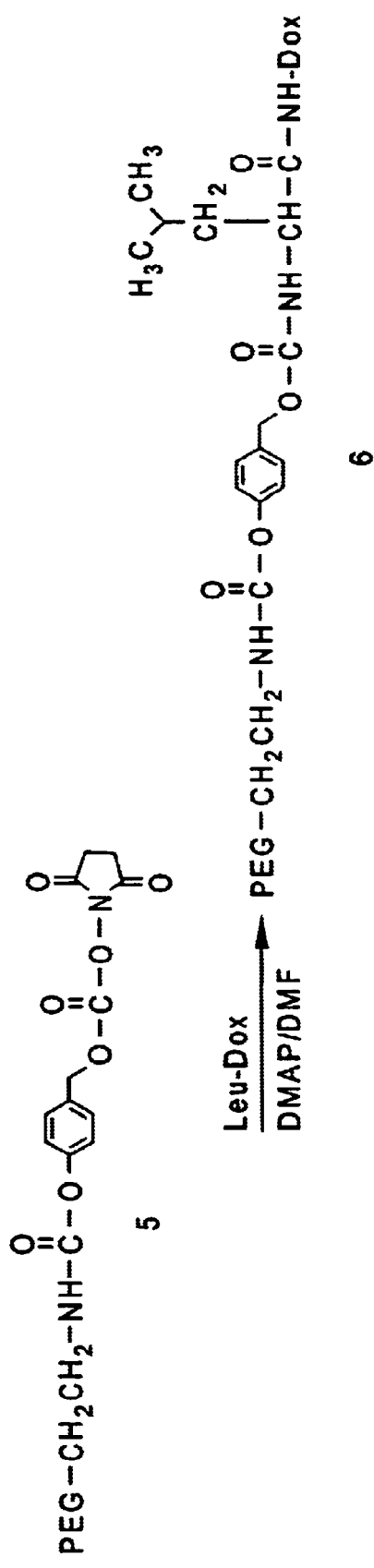
FIG. 5: Illustrates the synthesis of compound 6, as described by Example 2.
Figure 6:
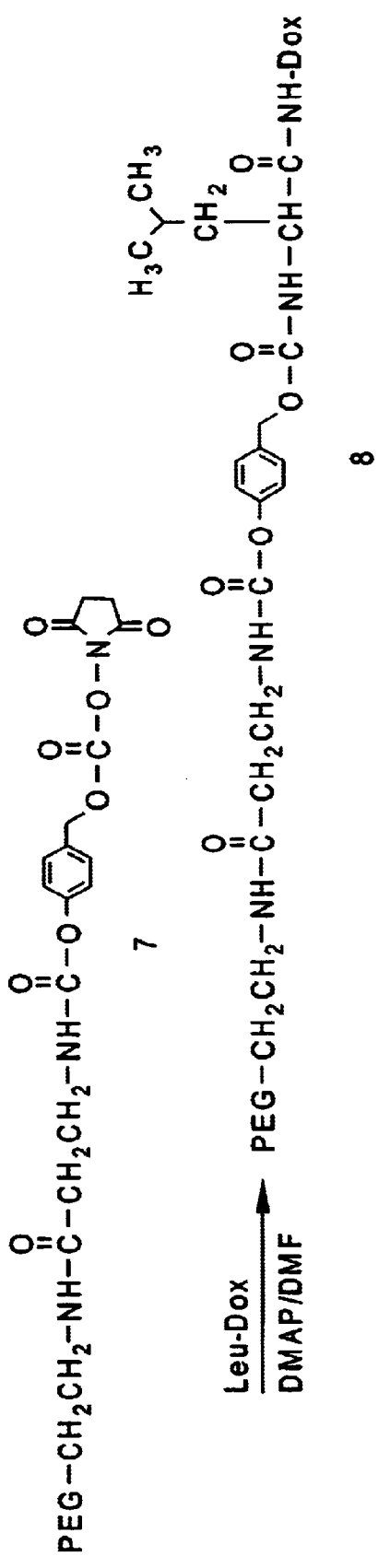
FIG. 6: Illustrates a schematic of the synthesis of compound 8, as described by Example 3.
Figure 7A:
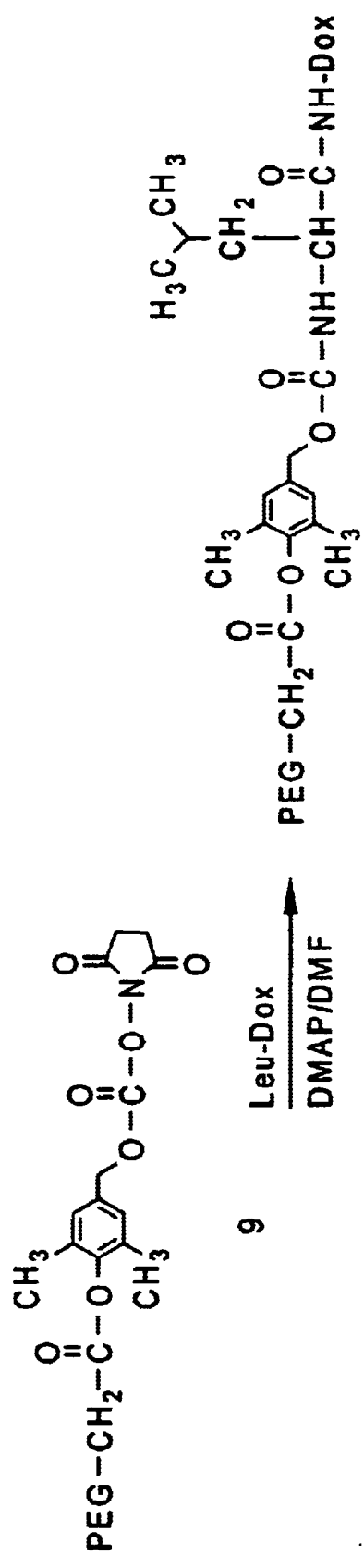
FIG. 7A: Illustrates a schematic of the synthesis of compound 10, as described by Example 4.
Figure 7B:
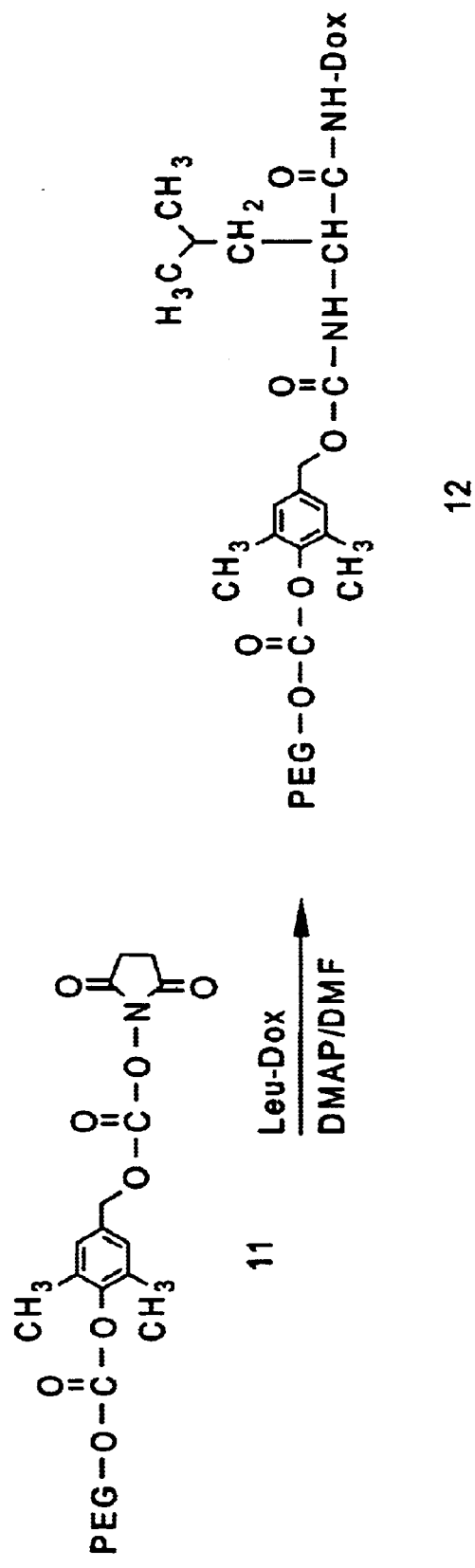
FIG. 7B: Illustrates a schematic of the synthesis of compound 12, as described by Example 5.
Figure 8:
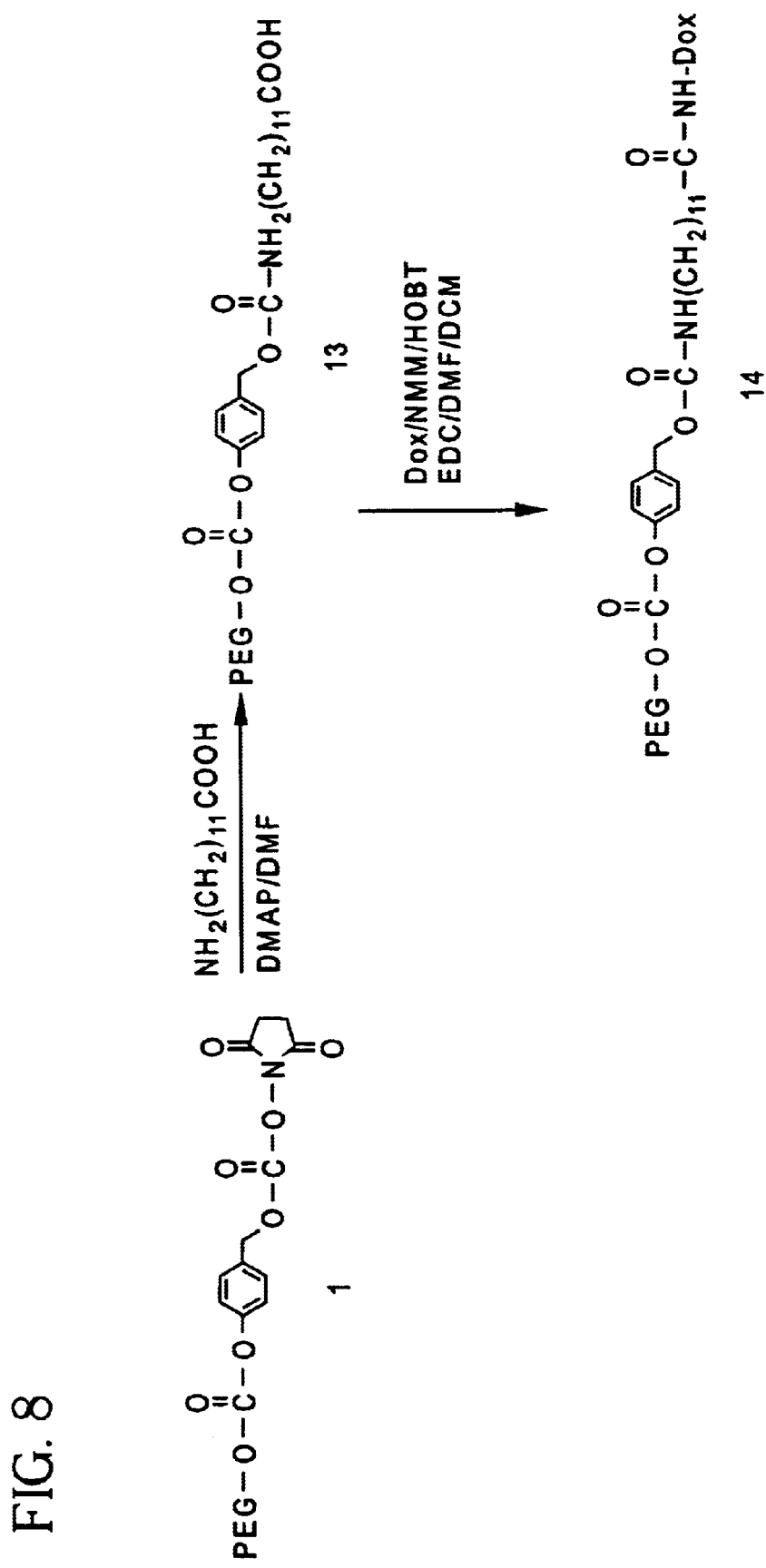
FIG. 8: Illustrates a schematic of the synthesis of compound 14, as described by Example 6.

With reference to FIGS. 2A and 2B, when Ar is a benzyl derivative, a 1,4 or 1,6-benzyl elimination (or an analogous reaction with other aromatic moieties) occurs in vivo and produces the desired transport-enhanced native compound by electron migration, causing irreversible decomposition, which releases the transport-enhanced native compound.

Thus, FIG. 2A illustrates, in overview, an in vivo degradation reaction is shown wherein the variables of the starting tetrapartate compound are defined as described supra for Formula I. With reference to FIG. 2, the illustrated tetrapartate prodrug undergoes a controllable rate cleavage, in vivo, labeled as (a) to remove $R_{11}$. The remaining compound (b) immediately undergoes a fast hydrolysis (c) in the presence of water to separate (b) and release Z—D, the enhancer-prodrug is released (d) mostly into the extracellular tissue space as Z—D. Z—D is, in turn, taken up by surrounding cells and hydrolyzed intracellularly (e) to release D. Any D that might be released in the intracellular tissue space is thought to be rapidly removed by blood or plasma flow, and is believed to provide little or no added benefit in terms of a therapeutic or diagnostic function.

In somewhat more detail, FIG. 2B provides schematics of in vivo degradation reactions thought to occur for compounds 14 and 17 (see, e.g., the Examples below for synthetic details). Analogously to the scheme of FIG. 2A, compound 14 is degraded by a controllable rate cleavage, in vivo, labeled as (a) to remove PEG. The remaining compound (b) immediately undergoes a fast hydrolysis (c) in the presence of water to separate (b) and release inter alia, (d) which is analogous to Z—D of FIG. 2A. The enhancer-doxorubicin prodrug is released mostly into the extracellular tissue space (d). The enhancer-doxorubicin prodrug is, in turn, taken up by surrounding cells and hydrolyzed intracellularly (e) to release active doxorubicin. An analogous degradation process is described in FIG. 2B for compound 17, wherein the analogous process steps are labeled as (a'), (b'), (c'), (d') and (e'). Reaction (f) and (f') refers to respective side reactions wherein the aromatic remainder that is cleaved from the prodrug is converted to a water soluble hydroxyl derivative.

E. Substantially Non-Antigenic Polymers

The "tetrapartate prodrug" compositions of the present invention include water-soluble polymer, $R_{11}$. Optionally, $R_{11}$ includes a capping group A. Capping group A includes, for example, hydrogen, $C_{1-6}$ alkyl moieties, carboxyalkyl, dialkyl acyl urea alkyls, and/or a compound of formula (II) shown below, which forms a bis-system:

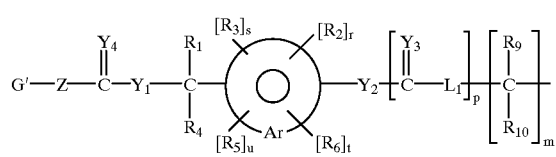

(II)

wherein G' is the same as D or another member of the group defined by D, v is 0 or 1, and the remaining variables are as set forth above with regard to Formula (I).

Suitable examples of such polymers include polyalkylene oxides such as polyethylene glycols which are also preferably substantially non-antigenic. The general formula for PEG and its derivatives, i.e. A'—O—(CH$_2$CH$_2$O)$_x$—(CH$_2$)$_n$—A, where (x) represents the degree of polymerization (i.e. 10–2,300) or number of repeating units in the polymer chain and is dependent on the molecular weight of the polymer; (n) is zero or a positive integer; A is a capping group as defined herein, i.e. an —H, amino, carboxy, halo, $C_{1-6}$ alkyl or other activating group and A' is the same as A or another A moiety. Also useful are polypropylene glycols, branched PEG derivatives such as those described in commonly-assigned U.S. Pat. No. 5,643,575, "star-PEG's" and multi-armed PEG's such as those described in Shearwater Polymers, Inc. catalog "Polyethylene Glycol Derivatives 1997–1998"; the disclosure of each is incorporated herein by reference. It will be understood that the water-soluble polymer will be functionalized for attachment to the linkage via M, X or Q herein. As an example, the PEG portion of the prodrugs can be the following non-limiting compounds:

—C(=Y$_7$)—(CH$_2$)$_n$—O—(CH$_2$CH$_2$O)$_x$—A,
—C(=Y$_7$)—Y$_7$—(CH$_2$)$_n$—O—(CH$_2$CH$_2$O)$_x$—A and
—C(=Y$_7$)—NR$_{12}$—(CH$_2$)$_n$—O—(CH$_2$CH$_2$O)$_x$—A, where $Y_7$ is O or S; and A, $R_{12}$, (n) and (x) are as defined above.

In many aspects of the present invention, polyethylene glycols (PEG's), mono-activated, $C_{1-4}$ alkyl-terminated PAO's such as mono-methyl-terminated polyethylene glycols (mPEG's) are preferred when mono-substituted polymers are desired; bis-activated polyethylene oxides are preferred when di-substituted prodrugs are desired.

In order to provide the desired hydrolyzable linkage, mono- or di-acid activated polymers such as PEG acids or PEG diacids can be used as well as mono-or di-PEG amines and mono- or di-PEG diols. Suitable PAO acids can be synthesized by first converting mPEG—OH to an ethyl ester followed by saponification. See also Gehrhardt, H., et al. Polymer Bulletin 18: 487 (1987) and Veronese, F. M., et al., J. Controlled Release 10; 145 (1989). Alternatively, the PAO-acid can be synthesized by converting mPEG—OH into a t-butyl ester followed by acid cleavage. See, for example, commonly assigned U.S. Pat. No. 5,605,976. The disclosures of each of the foregoing are incorporated by reference herein.

Although PAO's and PEG's can vary substantially in number average molecular weight, polymers ranging from about 2,000 to about 100,000 daltons are usually selected for the purposes of the present invention. Molecular weights of from about 20,000 to about 50,000 are preferred, and 20,000 to about 40,000 are particularly preferred. The number average molecular weight of the polymer selected for inclusion in the "tetrapartate prodrug" must be sufficient so as to provide sufficient circulation of the "tetrapartate prodrug" before removal of the transport enhancer. Within the ranges provided above, polymers having molecular weight ranges of at least 20,000 are preferred in some aspects for chemotherapeutic and organic moieties. In the case of some nucleophiles such as certain proteins, enzymes and the like, polymers having a molecular weight range of from about 12,000 to about 20,000 are preferred.

The polymeric substances included herein are preferably water-soluble at room temperature. A non-limiting list of such polymers include polyalkylene oxide homopolymers such as polyethylene glycol (PEG) or polypropylene glycols, polyoxyethylenated polyols, copolymers thereof and block copolymers thereof, provided that the water solubility of the block copolymers is maintained.

As an alternative to PAO-based polymers, effectively non-antigenic materials such as dextran, polyvinyl alcohols, carbohydrate-based polymers, hydroxypropylmethacrylamide (HPMA), and copolymers thereof, etc. and the like can be used if the same type of activation is employed as described herein for PAO's such as PEG. Those of ordinary skill in the art will realize that the foregoing list is merely illustrative and that all polymeric materials having the qualities described herein are contemplated. For purposes of the present invention, "effectively non-antigenic" means all polymeric materials understood in the art as being nontoxic and not eliciting an appreciable immune response in mammals.

F. Polymeric Tetrapartate Transport System Synthesis

Synthesis of representative, specific prodrugs is set forth in the Examples. Generally, however, the transport enhanced prodrugs of the present invention can be prepared in several fashions. Thus, one method includes reacting a compound of formula (III).

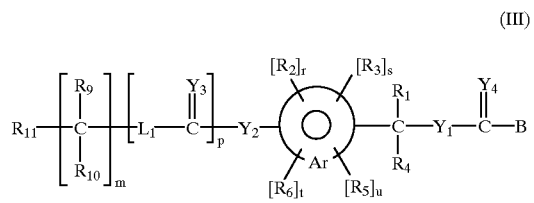

(III)

with a compound of the formula (IV): Lx—Z—[D]$_y$

In this embodiment, $L_1$ is a bifunctional linking moiety:
B and Lx are independently selected leaving groups and are defined as above for when D is a leaving group;

Z is a moiety that is actively transported into a target cell, a hydrophobic moiety and combinations thereof. Preferably, Z is selected from the group consisting of an amino acid residue, a $C_{6-18}$ alkyl, a substituted aryl, a hetero aryl, —C(=$Y_4$), —C(=S), —C(=$NR_{16}$) and combinations thereof, wherein $R_{16}$ is selected from the same group as $R_{12}$;

$R_1$, $R_4$, $R_9$, $R_{10}$ and $R_{12}$ are independently selected from the group consisting of hydrogen, $C_{1-6}$ alkyls, $C_{3-12}$ branched alkyls, $C_{3-8}$ cycloalkyls, $C_{1-6}$ substituted alkyls, $C_{3-8}$ substituted cycloalkyls, aryls, substituted aryls, aralkyls, $C_{1-6}$ heteroalkyls and substituted $C_{1-6}$ heteroalkyls;

$R_2$, $R_3$, $R_5$ and $R_6$ are independently selected from the group consisting of hydrogen, $C_{1-6}$ alkyls, $C_{1-6}$ alkoxys, phenoxy, $C_{1-8}$ heteroalkyls, $C_{1-8}$ heteroalkoxys, substituted $C_{1-6}$ alkyls, $C_{3-8}$ cycloalkyls, $C_{3-8}$ substituted cycloalkyls, aryls, substituted aryls, aralkyls, halo-, nitro- and cyano-, carboxy-, $C_{1-6}$ carboxyalkyls and $C_{1-6}$ alkylcarbonyls;

Ar is a moiety which when included in Formula (III), and subsequently in Formula (I), forms a multi-substituted aromatic hydrocarbon or a multi-substituted heterocyclic group;

(m), (r), (s), (t), and (u) are independently zero or one;

(p) is zero or a positive integer;

$Y_{1-4}$ are independently O, S, or $NR_{12}$, wherein the definition of $R_{12}$ is defined as per formula I, supra; (y) is one or two; and $R_{11}$ is a monovalent or divalent polymer residue.

Typically, the reaction between (III) and (IV) is conducted in the presence of a solvent and a base. The solvent is preferably an inert solvent, i.e., inert with respect to the reactants and products. Exemplary solvents include, simply by way of example, chloroform, toluene, methylene chloride, dimethylformamide and combinations thereof. Generally, dimethylformamide is preferred. Exemplary bases solvents include, simply by way of example, dimethylaminopyridine, diisopropylethylamine, pyridine, triethylamine and combinations thereof Generally, dimethylaminopyridine is preferred.

Optionally, the tetrapartate prodrugs of the invention can also be prepared by reacting a compound of formula (V)

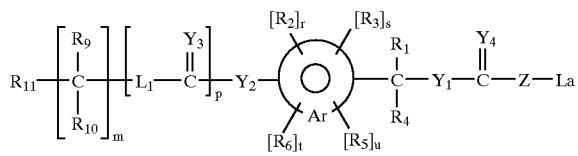

(V)

with a biologically effective material, e.g., a biologically active compound such as a drug or diagnostic tag. In this embodiment, La is a leaving group for Formula V as defined for D when D is a leaving group.

$L_1$ is a bifunctional linking moiety;

Z is a moiety that is actively transported into a target cell, a hydrophobic moiety and combinations thereof Preferably, Z is selected from the group consisting of an amino acid residue, a $C_{6-18}$ alkyl, a substituted aryl, a hetero aryl, —C(=$Y_4$), —C(=S), —C(=$NR_{16}$) and combinations thereof;

$R_1$, $R_4$, $R_9$, $R_{10}$, $R_{12}$ and $R_{16}$ are independently selected from the group consisting of hydrogen, $C_{1-6}$ alkyls, $C_{3-12}$ branched alkyls, $C_{3-8}$ cycloalkyls, $C_{1-6}$ substituted alkyls, $C_{3-8}$ substituted cycloalkyls, aryls, substituted aryls, aralkyls, $C_{1-6}$ heteroalkyls and substituted $C_{1-6}$ heteroalkyls;

$R_2$, $R_3$, $R_5$ and $R_6$ are independently selected from the group consisting of hydrogen, $C_{1-6}$ alkyls, $C_{1-6}$ alkoxys, phenoxy, $C_{1-8}$ heteroalkyls, $C_{1-8}$ heteroalkoxys, substituted $C_{1-6}$ alkyls, $C_{3-8}$ cycloalkyls, $C_{3-8}$ substituted cycloalkyls, aryls, substituted aryls, aralkyls, halo-, nitro- and cyano-, carboxy-, $C_{1-6}$ carboxyalkyls and $C_{1-6}$ alkylcarbonyls.

Ar is a moiety which when included in Formula (V) forms a multi-substituted aromatic hydrocarbon or a multi-substituted heterocyclic group.

(m), (r), (s), (t), and (u) are independently zero or one.

(p) is zero or a positive integer.

$Y_{1-4}$ are independently O, S, or $NR_{12}$, wherein the definition of $R_{12}$ is defined as per formula I, supra; and $R_{11}$ is a monovalent or divalent polymer residue.

Optionally, the reaction between (V) and the biologically effective material is conducted in the presence of a coupling agent, including, for example, 1,3-diisopropylcarbodiimide, a dialkyl carbodiimides, 2-halo-1-alkyl-pyridinium halide, 1-(3-dimethylamino-propyl)-3-ethyl carbodiimide, 1-propanephosphonic acid cyclic anhydride, phenyl dichlorophosphates, and combinations thereof. In addition, the reaction between (V) and the biologically active material is typically conducted in the presence of a solvent and a base, each of which are defined as described supra, for the reaction between formulas (III) and (IV). In addition, the base is preferably dimethylamino pyridine.

Biologically effective materials for the tetrapartate prodrug are discussed below.

G. Leaving Groups or Residue Portion "D"

1. Leaving Groups

In those aspects where B is a leaving group and further with reference to the Lz and/or La leaving groups, as described above, suitable leaving groups include, without limitations, moieties such as N-hydroxybenzotriazolyl, halogen, N-hydroxyphthalimidyl, p-nitrophenoxy, imidazolyl, N-hydroxysuccinimidyl; thiazolidinyl thione, or other good leaving groups as will be apparent to those of ordinary skill. The synthesis reactions used and described herein will be understood by those of ordinary skill without undue experimentation.

For example, the acylated intermediate compound (III) can be reacted with such as 4-nitrophenyl chloroformate, disuccinimidyl carbonate (DSC), carbonyldiimidazole, thiazolidine thione, etc. to provide the desired activated derivative.

The acylation of the p-hydroxybenzyl alcohol or the p-aminobenzyl alcohol and the o-hydroxbenzyl alcohol or the o-aminobenzyl alcohol can be carried out with, for example, thiazolidine thione activated polymers, succinimidyl carbonate activated polymers, carboxylic acid activated polymers, blocked amino acid derivatives.

Once in place, the "activated" form of the PEG prodrug (or blocked prodrug) is ready for conjugation with an amine- or hydroxyl-containing compound. Some preferred activated transport forms are shown below.

2. Residues of Biologically Active Materials

Broadly, the only limitations on the types of biologically effective materials suitable for inclusion herein is that there is available at least one site for covalent attachment to the uptake enhancer moiety. Simply by way of example, this can be a (primary or secondary) amine-containing position or functional group which can react and link with a carrier portion, e.g., by forming an amide bond. Other sites for covalent attachment to the uptake enhancer moiety include, e.g., a hydroxyl functional group, to form, e.g., an ester linkage. Of course, the artisan will appreciate that the selected linkage between the biologically effective material of interest, and the uptake enhancer is such that there is no substantial loss of bioactivity after the double prodrug portion of the conjugate releases the parent compound in linkage with a transport enhancer.

After conjugation, the remaining amine-containing compound is referred to as the residue of the unconjugated compound.

I. Residues of Amine-containing Compounds

In some aspects of the invention, e.g., after the prodrug transport has been formed, D is a residue of an amine-containing organic compound. Organic compounds include, without limitation, moieties such as anthracycline compounds including daunorubicin, doxorubicin; p-aminoaniline mustard, melphalan, Ara-C (cytosine arabinoside) and related anti-metabolite compounds, e.g., gemcitabine, etc.

Also included herein is any portion of a polypeptide, nucleic acid, peptide nucleic acids and any combinations thereof, ranging in size from about 50 daltons through about 2,500 daltons, or greater, demonstrating in vivo bioactivity. This includes, e.g., peptides, nucleic acids (DNA, RNA) with at least one amine functional group, e.g., peptide nucleic acids and the like.

Thus, in a preferred aspect of the invention, biologically effective material is a biologically active compound that is suitable for medicinal or diagnostic use in the treatment of animals, e.g., avians and/or mammals, including humans, for conditions for which such treatment is desired. The foregoing list of biological materials is meant to be illustrative and not limiting for the compounds which can be modified. Those of ordinary skill will realize that other such compounds can be similarly modified without undue experimentation. It is to be understood that those biologically active materials not specifically mentioned but having suitable amino-groups are also intended and are within the scope of the present invention.

II. Residues of Hydroxyl-Containing Compounds a. Camptothecin and Related Topoisomerase I Inhibitors Camptothecin is a water-insoluble cytotoxic alkaloid produced by Camptotheca accuminata trees indigenous to China and nothapodytes foetida trees indigenous to India. Camptothecin and related compounds and analogs are also known to be potential anticancer or antitumor agents and have been shown to exhibit these activities in vitro and in vivo. Camptothecin and related compounds are also candidates for conversion to the tetrapartate prodrugs of the present invention.

Camptothecin and certain related analogues share the structure:

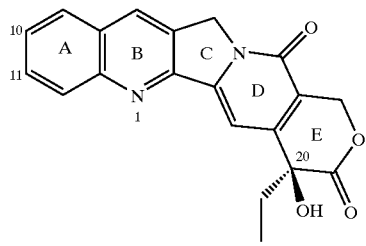

From this core structure, several known analogs have been prepared. For example, the A ring in either or both of the 10- and 11-positions can be substituted with an OH. The A ring can also be substituted in the 9-position with a straight or branched $C_{1-30}$ alkyl or $C_{1-17}$ alkoxy, optionally linked to the ring by a heteroatom i.e. —O or S. The B ring can be substituted in the 7-position with a straight or branched $C_{1-30}$ alkyl or substituted alkyl-, $C_{5-8}$ cycloalkyl, $C_{1-30}$ alkoxy, phenyl alkyl, etc., alkyl carbamate, alkyl carbazides, phenyl hydrazine derivatives, amino-, aminoalkyl-, aralkyl, etc. Other substitutions are possible in the C, D and E rings.

See, for example, U.S. Pat. Nos. 6,111,107; 5,004,758; 4,943,579; Re 32,518, the contents of which are incorporated herein by reference. Such derivatives can be made using known synthetic techniques without undue experimentation. Preferred camptothecin derivatives for use herein include those which include a 20-OH or another OH moiety which is capable of reacting directly with activated forms of the polymer transport systems described herein or to the linking moiety intermediates, e.g. iminodiacetic acid, etc., which are then attached to a polymer such as PEG.

Reference to camptothecin analogs herein has been made for purposes of illustration and not limitation.

b. Taxanes and Paclitaxel Derivatives

One class of compounds included in the tetrapartate prodrug compositions of the present invention is taxanes. For purposes of the present invention, the term "taxane" includes all compounds within the taxane family of terpenes. Thus, taxol (paclitaxel), 3'-substituted tert-butoxy-carbonyl-amine derivatives (taxoteres) and the like as well as other analogs which are readily synthesized using standard organic techniques or are available

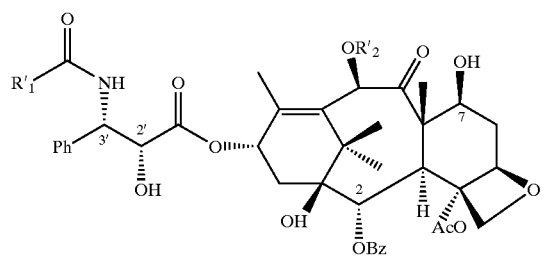

from commercial sources such as Sigma Chemical of St. Louis, Mo. are within the scope of the present invention. Representative taxanes are shown below.

Paclitaxel: $R'_1$=$C_6H_5$; $R'_2$=$CH_3CO$; Taxotere: $R'_1$=$(CH_3)_3CO$; $R'_2$=H These derivatives have been found to be effective anti-cancer agents. Numerous studies indicate that the agents have activity against several malignancies. To date, their use has been severely limited by, among other things, their short supply, poor water solubility and hypersensitivity. It is to be understood that other taxanes including the 7-aryl-carbamates and 7-carbazates disclosed in commonly assigned U.S. Pat. Nos. 5,622,986 and 5,547,981 can also be included in the tetrapartate prodrugs of the present invention. The contents of the foregoing U.S. patents are incorporated herein by reference. The only limitation on the taxane is that it must be capable of undergoing a hydroxyl based substitution reaction such as at the 2' position. Paclitaxel, however, is a preferred taxane.

c. Additional Biologically-Active Moieties

In addition to the foregoing molecules, the tetrapartate prodrug formulations of the present invention can be prepared using many other compounds. For example, drugs such as gemcitabine, etoposide, triazole-based antifungal agents such as fluconazole and/or ciclopirox can be used.

The parent compounds selected for tetrapartate prodrug forms need not be substantially water-insoluble, although the polymer-based tetrapartate prodrugs of the present invention are especially well suited for delivering such water-insoluble compounds. Other useful parent compounds include, for example, certain low molecular weight biologically active proteins, enzymes and peptides, including peptido glycans, as well as other anti-tumor agents; cardiovascular agents such as forskolin; anti-neoplastics such as combretastatin, vinblastine, doxorubicin, ara-C, maytansine, etc.; anti-infectives such as vancomycin, erythromycin, etc.; anti-fungals such as nystatin, amphoteracin B, triazoles, papulocandins, pneumocandins, echinocandins, polyoxins, nikkomycins, pradimicins, benanomicins, etc. see, "Antibiotics That Inhibit Fungal Cell Wall Development" *Annu. Rev. Microbiology*, 1994, 48:471–97, the contents of which are incorporated herein by reference; anti-anxiety agents, gastrointestinal agents, central nervous system-activating agents, analgesics, fertility or contraceptive agents, anti-inflammatory agents, steroidal agents, anti-urecemic agents, cardiovascular agents, vasodilating agents, vasoconstricting agents and the like.

After conjugation, the remaining amine-or hydroxyl-containing compound is referred to as the residue of the unconjugated compound.

3. Polymeric Hybrids

In another aspect of the invention there are provided hybrid types of the polymeric tetrapartate prodrug transport system described herein. In particular, the hybrid system includes not only the reversible double prodrug system described above but also a second polymeric transport system based on more permanent types of linkages. The hybrids can be prepared by at least two methods. For example, the benzyl-elimination-based prodrug can be synthesized first and then PEGylated using any art-recognized activated polymer such as thiazolidinyl thione-or succinimidyl carbonate-activated PEG. Alternatively, the more permanent conjugation reaction can be performed first and the resultant conjugates can be used to form the double prodrug portion of the tetrapartate conjugates described herein. It will be understood that the hybrid systems will be better suited for proteins, enzymes and the like where multiple amino groups are available for attachment of the polymeric transport forms. For purposes of the present invention, "activated polymers" will be understood to include polymers containing one or more terminal groups which are capable of reacting with one or more of α-amino groups, ε-amino groups, histidine nitrogens, carboxyl groups, sulfhydryl groups, etc. found on enzymes, proteins, etc., as well as such groups found on synthetically prepared organic compounds. It will further be appreciated that the activating groups described below can also be used to form the activated transport forms described above.

The activating terminal moiety can be any group which facilitates conjugation of the polymers with the biologically active material, i.e., protein, enzyme, etc. either before of after the double prodrug transport system of the present invention has been synthesized. See, for example, U.S. Pat. No. 4,179,337, the disclosure of which is hereby incorporated by reference. Such activating groups can be a moiety selected from:

I. Functional groups capable of reacting with an amino group such as:
 a) carbonates such as the p-nitrophenyl, or succinimidyl; see, for example, U.S. Pat. No. 5,122,614, the disclosure of which is hereby incorporated by reference;
 b) carbonyl imidazole;
 c) azlactones; see, for example, U.S. Pat. No. 5,321,095, the disclosure of which is hereby incorporated by reference;
 d) cyclic imide thiones see, for example, U.S. Pat. No. 5,349,001, the disclosure of which is hereby incorporated by reference;
 e) isocyanates or isothiocyanates; or
 f) active esters such as N-hydroxy-succinimidyl or N-hydroxybenzotriazolyl.

II. Functional groups capable of reacting with carboxylic acid groups and reactive carbonyl groups such as:
 a) primary amines; or
 b) hydrazine and hydrazide functional groups such as the acyl hydrazides, carbazates, semicarbamates, thiocarbazates, etc.

III. Functional groups capable of reacting with mercapto or sulfhydryl groups such as phenyl glyoxals; see, for example, U.S. Pat. No. 5,093,531, the disclosure of which is hereby incorporated by reference;

IV. Functional groups capable of reacting with hydroxyl groups such as (carboxylic) acids or other nucleophiles capable of reacting with an electrophilic center. A non-limiting list includes, for example, hydroxyl, amino, carboxyl, thiol groups, active methylene and the like.

The activating moiety can also include a spacer moiety located proximal to the polymer. The spacer moiety may be a heteroalkyl, alkoxy, alkyl containing up to 18 carbon atoms or even an additional polymer chain. The spacer moieties can added using standard synthesis techniques.

H. Methods of Treatment

Broadly, another aspect of the present invention provides methods for delivering biologically active materials, such as therapeutic or diagnostic agents into cells where such biological activity is desired. While the tetrapartate prodrugs of the invention are readily employed to deliver biologically active materials into a wide variety of cells, found throughout the animal body, certain applications are preferred. For example, the tetrapartate prodrugs of the invention are particularly useful in delivering biologically active materials, such as drugs and/or diagnostics, into cells present in tissues exhibiting the above-discussed EPR effect. A number of tissue types exhibiting EPR occur in different diseases and disorders, including tissues undergoing inflammation, toxic reactions of various kinds, as well as solid tumors.

Thus, the broad method includes contacting living tissue with the inventive tetrapartate prodrugs. Preferably the tissue exhibits the EPR effect, so that polymer linked conjugates preferably enter such tissues. Of course, the artisan will appreciate that an agent, once delivered into a target cell and activated, can then be released by that cell and provide biological activity in other tissue spaces.

Simply by way of example, a non-active prodrug of the invention that is delivered into an exocrine cell of the liver or pancreas under suitable conditions, e.g., during a disease process that causes inflammation, and results in an EPR effect, can be activated within the cytoplasm of the target cell, and then the activated drug or diagnostic agent can then be secreted into the gastrointestinal ("G.I") tract fluid space for therapeutic and/or diagnostic purposes. In this instance, treatment and/or diagnosis of certain diseases or disorders of the G.I. tract by means of the targeted delivery of appropriate agents, including anti-cancer or antiviral agents, is therefore facilitated. Analogous methods of treatment and delivery of biologically active materials is readily contemplated for other organ and/or tissue systems.

In one preferred embodiment, the tissues are tumor or cancer tissues, and the tetrapartate prodrugs of in the invention comprise agents suitable for treatment and/or diagnosis of such conditions. Thus, the tetrapartate prodrug compositions are useful for, among other things, treating diseases which are similar to those which are treated with the parent compound(s), e.g., including compounds suitable for treating neoplastic disease, reducing tumor burden, inhibiting metastasis of tumors or neoplasms and preventing recurrences of tumor/neoplastic growths in mammals. The treated animals are preferably mammals, and more preferably human patients. While veterinary use of the prodrugs of the invention will typically be employed in mammalian species, it is further contemplated that the prodrugs can also be readily employed in other species generally within the veterinary practice and animal husbandry arts, e.g., including highly valued non-mammalian exotic animals.

The amount of the prodrug and/or diagnostic tetrapartate tag that is administered will depend upon the amount of the parent molecule included therein. Generally, the amount of tetrapartate prodrug used in the treatment methods is that amount which effectively achieves the desired therapeutic or diagnostic result in mammals. Naturally, the dosages of the various prodrug compounds will vary somewhat depending upon the parent compound, rate of in vivo hydrolysis, molecular weight of the polymer, etc. In general, tetrapartate prodrug polymeric derivatives are administered in amounts ranging from about 5 to about 500 mg/m$_2$ per day, based on the native drug. The range set forth above is illustrative and those skilled in the art will determine the optimal dosing of the prodrug selected based on clinical experience and the treatment indication. Actual dosages will be apparent to the artisan without undue experimentation.

The compositions, including prodrugs, of the present invention can be included in one or more suitable pharmaceutical compositions for administration to an animal in need thereof. The pharmaceutical compositions may be in the form of a solution, suspension, tablet, capsule or the like, prepared according to methods well known in the art. It is also contemplated that administration of such compositions may be by the oral and/or parenteral routes depending upon the needs of the artisan. A solution and/or suspension of the composition may be utilized, for example, as a carrier vehicle for injection or infiltration of the composition by any art known methods, e.g., by intravenous, intramuscular, subdermal injection and the like.

Such administration may also be by infusion into a body space or cavity, as well as by inhalation and/or intranasal routes. In preferred aspects of the invention, however, the prodrugs are parenterally administered to animals in need thereof.

The novel methods of treatment or administration according to the invention further includes the multi-step cleavage of the prodrug, resulting in release of the biologically active material, such as a drug or tag, within a target cell.

I. In vivo Diagnostics

A further aspect of the invention provides the tetrapartate conjugates of the invention optionally prepared with a diagnostic tag linked to the transport enhancer described above, wherein the tag is selected for diagnostic or imaging purposes. Thus, a suitable tag is prepared by linking any suitable moiety, e.g., an amino acid residue, to any art-standard emitting isotope, radio-opaque label, magnetic resonance label, or other non-radioactive isotopic labels suitable for magnetic resonance imaging, fluorescence-type labels, labels exhibiting visible colors and/or capable of fluorescing under ultraviolet, infrared or electrochemical stimulation, to allow for imaging tumor tissue during surgical procedures, and so forth. Optionally, the diagnostic tag is incorporated into and/or linked to a conjugated therapeutic moiety, allowing for monitoring of the distribution of a therapeutic biologically active material within an animal or human patient.

In a still further aspect of the invention, the inventive tagged tetrapartate conjugates are readily prepared, by art-known methods, with any suitable label, including, e.g., radioisotope labels. Simply by way of example, these include $^{131}$Iodine, $^{125}$Iodine, $^{99m}$Technetium and/or $^{111}$Indium to produce radioimmunoscintigraphic agents for selective uptake into tumor cells, in vivo. For instance, there are a number of art-known methods of linking peptide to Tc-99 m, including, simply by way of example, those shown by U.S. Pat. Nos. 5,328,679; 5,888,474; 5,997,844; and 5,997,845, incorporated by reference herein.

Broadly, for anatomical localization of tumor tissue in a patient, the tetrapartate conjugate tag is administered to a patient or animal suspected of having a tumor. After sufficient time to allow the labeled immunoglobulin to localize at the tumor site(s), the signal generated by the label is detected, for instance, visually, by X-ray radiography, computerized transaxial tomography, MRI, by instrumental detection of a luminescent tag, by a photo scanning device such as a gamma camera, or any other method or instrument appropriate for the nature of the selected tag.

The detected signal is then converted to an image or anatomical and/or physiological determination of the tumor site. The image makes it possible to locate the tumor in vivo and to devise an appropriate therapeutic strategy. In those embodiments where the tagged moiety is itself a therapeutic agents, the detected signal provides evidence of anatomical localization during treatment, providing a baseline for follow-up diagnostic and therapeutic interventions.

J. EXAMPLES

It should be noted for all of the compounds that were produced by the following examples, and as illustrated by FIGS. 1–9, that "PEG" is:

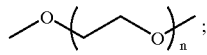

although other art-known variations are readily employed, as mentioned supra. In addition, the PEG employed in the following examples had a molecular weight of about 40 kDa.

The following examples serve to provide further appreciation of the invention but are not meant in any way to restrict the effective scope of the invention.

Example 1

Synthesis of Compound 2

Compound 2 (FIG. 3) was Prepared by One of the Following Methods

Method 1

Leucine-doxorubicin (130 mg, 0.198 mmol) and dimethylaminopyridine ("DMAP," 121 mg, 0.99 mmol) were added to a solution of compound 1, having a PEG chain of about 40 kDa (2.4 g, 0.060 mmol, FIG. 1) in 40 mL of anhydrous dimethyformamide ("DMF"). The mixture was stirred at room temperature overnight. Ethyl ether (~200 mL) was added to the reaction mixture to precipitate PEG derivatives, and the solid filtered and recrystallized twice from from 80 mL 2-propanol ("IPA") to give pure product of compound 2 (1.85 g, 75%, FIG. 3).

Method 2

(Step 1) To a solution of compound 1 (4.5 g, 0.111 mmol, FIG. 4) in 80 mL of anhydrous methylene chloride, was added leucine t-butyl ester (248 mg, 1.11 mmol) and DMAP (136 mg, 1.11 mmol). The reaction mixture was stirred for 18 hours at room temperature. The mixture was evaporated under reduced pressure, and the residue was re-crystallized from IPA to give compound 3 (4.5 g, 99%, FIG. 4). The structure was confirmed by $^{13}$C NMR (67.8 MHz, CDCl$_3$) with peaks at δ171.55, 155.24, 152.88, 150.24, 133.79, 128.68, 120.48, 81.05, 69.0–72.5 (PEG), 52.51, 41.26, 27.40, 24.19, 22.27, 21.44.

(Step 2) compound 3 (4.70 g, 0.114 mmol) was dissolved in 22.5 mL trifluoroacetic acid and 45 mL of methylene chloride and stirred at room temperature for 2 hours. Ethyl ether was added to precipitate the PEG derivative. The crude product was filtered and washed with ethyl ether to yield compound 4 (4.4 g, 94%, FIG. 4). The structure was confirmed by $^{13}$C NMR (67.8 MHz, CDCl$_3$) with peaks at δ173.30, 155.36, 152.94, 150.24, 133.81, 128.67, 120.52, 69.0–72.5 (PEG), 52.65, 41.20, 24.18, 22.44, 21.31.

(Step 3) Doxorubicin (57 mg, 0.0984 mmol) and DMAP (42 mg, 0.344 mmol) were added to a solution of compound 4 (1.0 g, 0.0246 mmol, FIG. 4) in anhydrous methylene chloride (20 mL) at 0° C. for 20 minutes. 1-[3-(dimethylamino) propyl]-3-ethylcarbodiimide hydrochloride ("EDC," 28 mg, 0.148 mmol) was added, and the reaction mixture gradually warmed to room temperature and stirred overnight. The solution was filtered by gravity, and the solvent evaporated. The residual solid was recrystallized from IPA (50 mL) to give pure compound 2 (0.656 g, 67%). The structure was confirmed by $^{13}$C NMR (67.8 MHz, CDCl$_3$) with peaks at δ213.56, 186.82, 186.50, 171.27, 160.76, 155.93, 155.50, 153.21, 150.51, 135.55, 135.22, 133.84, 133.47, 129.05, 120.81, 119.53, 118.24, 111.26, 111.00, 100.40, 69.0–72.5 (PEG), 68.43, 67.46, 67.16, 65.86, 56.41, 53.39, 45.15, 41.40, 35.23, 29.21, 24.35, 22.72, 21.57, 16.61.

Example 2

Synthesis of Compound 6

Compound 6 (FIG. 5), was prepared by adding leucine-doxorubicin (130 mg, 0.198 mmol, FIG. 3) and DMAP (121 mg, 0.99 mmol) to a solution of compound 5 (2.2 g, 0.054 mmol, FIG. 5) in anhydrous DMF (30 mL). After stirring at room temperature overnight, ethyl ether (~100 mL) was added to the reaction mixture and the precipitated solid filtered. The solid was recrystallized twice from IPA (70 mL) to give pure product (2.09 g, 93%).

The structure was confirmed by $^{13}$C NMR (67.8 MHz, CDCl$_3$) with peaks at: δ213.40, 186.56, 186.23, 171.23, 160.61, 155.83, 155.65, 155.23, 154.25, 150.51, 135.41, 134.99, 133.43, 133.25, 132.79, 128.85, 121.26, 120.40, 119.36, 118.17, 111.06, 110.88, 100.34, 69.0–72.5 (PEG), 68.33, 67.10, 65.89, 65.08, 56.28, 53.27, 45.03, 41.20, 40.61, 40.41, 35.33, 33.50, 29.07, 24.23, 22.65, 21.40, 16.52.

Example 3

Synthesis of Compound 8

Compound 8 (FIG. 6), was prepared by the methods described in Example 2, above: by adding leucine-doxorubicin (80 mg, 0.122 mmol ) to a solution of compound 7 (1.6 g, 0.41 mmol, FIG. 4) in 30 mL of anhydrous DMF, and reacting the mixture to give the product 8, (1.44 g, 85%) which was recrystallized from IPA.

The structure was confirmed by $^{13}$C NMR (67.8 MHz, CDCl$_3$) with peaks at: δ213.64, 186.80, 186.42, 171.32, 171.21, 160.76, 155.97, 155.41, 154.30, 150.68, 135.54, 135.19, 133.50, 133.38, 129.06, 127.52, 121.41, 119.54, 118.25, 111.26, 111.06, 100.47, 69.0–72.5 (PEG), 68.54, 67.20, 66.13, 65.25, 56.43, 53.48, 45.11, 41.24, 38.97, 37.10, 35.40, 35.06, 33.64, 29.25, 24.39, 22.75, 21.55, 16.64.

Example 4

Synthesis of Compound 10

Compound 10 (FIG. 7A) was prepared by the methods described in Example 2, above: by adding leucine-doxorubicin (97 mg, 0.147 mmol, FIG. 7A) to a solution of compound 9 (2.0 g, 0.049 mmol, FIG. 7A) in 30 mL of anhydrous DMF. Pure compound 10 was obtained by recrystallization from IPA (1.70 g, 83%).

The structure was confirmed by $^{13}$C NMR (67.8 MHz, CDCl$_3$) with peaks at: δ213.71, 186.93, 186.55, 171.35, 168.14, 160.88, 156.03, 155.51, 135.61, 135.31, 133.67, 133.50, 130.08, 128.38, 120.69, 119.64, 118.31, 111.38, 111.19, 100.50, 69.0–72.5 (PEG), 68.64, 67.13, 66.28, 65.33, 56.51, 53.60, 45.23, 41.43, 35.50, 33.80, 29.47, 24.49, 22.79, 21.68, 16.69.

Example 5

Synthesis of Compound 12

Compound 12 (FIG. 7B), was prepared by the methods described in Example 2, above: by adding leucine-doxorubicin (134 mg, 0.204 mmol, FIG. 7B) to a solution of compound 11 (2.0 g, 0.049 mmol) ) in 30 mL of anhydrous DMF. Compound 12 was purified by recrystallization from IPA (1.69 g, 82%).

Example 6

Synthesis of Compound 14

Compound 14 (FIG. 8), was prepared as follows.

(Step 1) To a solution of compound 1 (6.88 g, 0.170 mmol, FIG. 8), in 90 mL anhydrous DMF, was added 12-aminododecanoic acid (0.15 g, 0.680 mmol) and DMAP (0.114 g, 0.934 mmol). The resulting reaction mixture was stirred for 18 hours at a temperature between 50 to 60° C. The mixture was filtered, the filtrate evaporated under reduced pressure, and the residue recrystallized from IPA to give compound 13 (6.2 g, 90). The structure was confirmed by $^{13}$C NMR (67.8 MHz, CDCl$_3$) with peaks at δ174.58, 155.79, 152.97, 150.20, 134.19, 128.77, 127.31, 120.52, 69.0–72.5 (PEG), 40.54, 33.32, 29.42, 28.90, 28.70, 28.59, 26.17, 24.87, 24.36.

(Step 2) To a solution of compound 13 (3.0 g, 0.074 mmol) as obtained in Step 1, above, doxorubicin hydrochloride (256 mg, 0.441 mmol), 4-methylmorpholine ("NMM", 130 uL, 1.18 mmol), and 1-hydroxybenzotriazole hydrate ("HOBT", 60 mg, 0.441 mmol) in 80 mL anhydrous DMF/methylene chloride (1:1) was EDC (113 mg, 0.589 mmol), and the mixture stirred at room temperature overnight. The solvent was evaporated under reduced pressure and the residue was recrystallized from IPA (100 mL) to give pure compound 14 (2.80 g, 91%)).

The structure was confirmed by $^{13}$C NMR (67.8 MHz, CDCl$_3$), with peaks at δ213.40, 186.56, 186.18, 172.11, 160.56, 155.97, 155.83, 155.22, 153.04, 150.26, 135.41, 134.96, 134.23, 133.45, 133.26, 128.83, 127.38, 120.60, 120.38, 118.14, 111.00, 110.81, 100.50, 69.0–72.5 (PEG), 68.28, 67.28, 67.04, 65.89, 65.02, 56.26, 44.61, 40.60, 40.41, 35.88, 35.26, 33.43, 29.46, 29.30, 28.93, 28.86, 26.20, 25.12, 16.55.

Example 7

Synthesis of Compound 17

Figure 9:
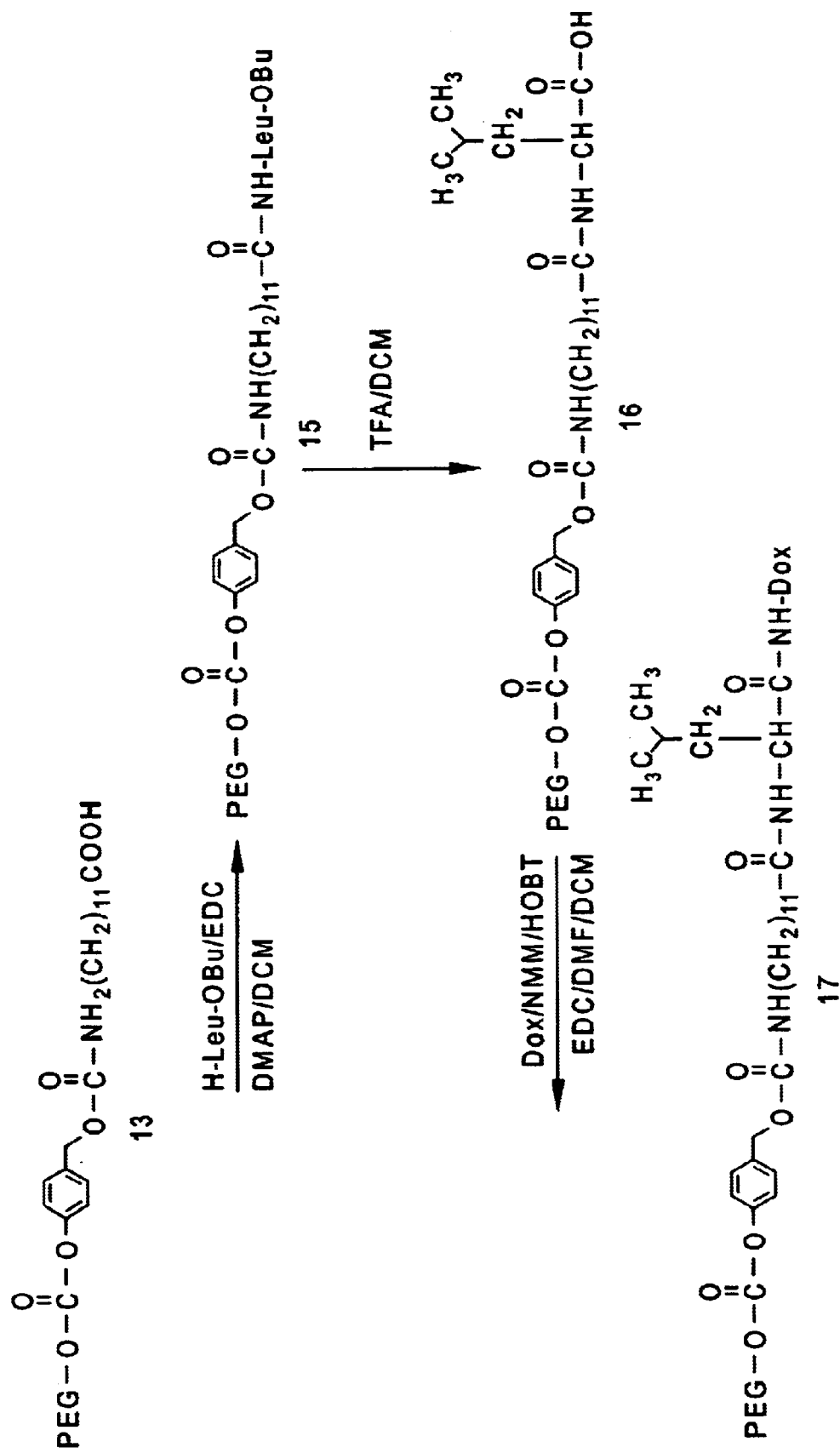
FIG. 9: Illustrates a schematic of the synthesis of compound 17, as described by Example 7.

Compound 17 was prepared as illustrated by FIG. 9.

(Step 1) To a solution of compound 13 (5.20 g, 0.128 mmol) in 50 mL anhydrous methylene chloride was added leucine t-butyl ester (0.287 g, 1.28 mmol), DMAP (0.281 g, 2.30 mmol), and EDC (0.197 g, 1.02 mmol). The reaction mixture was stirred at room temperature for 18 hours. Solvent was removed under reduced pressure, and the residue recrystallized from IPA to yield 15 (4.8 g, 92%, FIG. 9). The structure was confirmed by $^{13}$C NMR (67.8 MHz, CDCl$_3$) with peaks at δ172.22, 171.87, 155.79, 152. 98, 150.22, 134.20, 128.78, 120.54, 69.0–72.5 (PEG), 50.62, 41.37, 40.55, 35.96, 29.43, 28.88, 28.73, 27.49, 26.19, 25.05, 24.89, 24.39, 22.32, 21.65.

(Step 2) compound 15 (4.70 g, 0.114 mmol) was dissolved in 25 mL trifluoroacetic acid and 50 mL methylene chloride and stirred at room temperature for 2 hours. Ethyl ether was added to precipitate PEG product. The solid was filtered and washed with additional ethyl ether to yield compound 16 (4.4 g, 94%, FIG. 9). The structure was confirmed by $^{13}$C NMR (67.8 MHz, CDCl$_3$) with peaks at δ173.50, 172.50, 155.83, 153.01, 150.22, 134.20, 128.80, 120.55, 69.0–72.5 (PEG), 49.85, 41.16, 40.57, 35.91, 29.43, 28.84, 28.66, 26.17, 25.04, 24.35, 24.47, 21.52.

(Step 3) To a solution of compound 16 (3.3 g, 0.080 mmol), doxorubicin hydrochloride (280 mg, 0.480 mmol), NMM (130 uL, 1.18 mmol), and HOBT (74 mg, 0.480 mmol) in 90 mL of anhydrous DMF and methylene chloride (1:1) was added EDC (120 mg, 0.640 mmol), and the mixture stirred at room temperature overnight. The solvent was evaporated under reduced pressure and the residual solid was recrystallized from IPA (100 mL) to give pure compound 17 (2.90 g, 85%).

The structure was confirmed by $^{13}$C NMR (67.8 MHz, CDCl$_3$) with peaks at δ213.30, 186.44, 186.16, 172.77, 171.23, 160.55, 155.75, 155.13, 153.04, 150.26, 135.37, 134.91, 134.22, 133.38, 133.19, 128.81, 127.38, 120.58, 120.38, 119.27, 118.14, 110.97, 110.79, 100.24, 69.0–72.5 (PEG), 68.26, 67.27, 67.01, 65.10, 56.21, 51.11, 45.08, 41.02, 40.60, 35.91, 35.23, 33.39, 29.43, 28.90, 28.69, 26.22, 25.05, 24.23, 22.58, 21.61, 16.48.

Example 8

Confirmation of Efficacy of Tetrapartate Prodrug Relative to Doxorubicin

The efficacy of PEG-leu-doxorubicin analogs against a subcutaneous human ovarian carcinoma (A2780) injected into nude mice was determined as follows.

Following at least one week of acclimation, tumors were established in nude mice by injecting 1×10$^6$ (100,000) harvested A2780 ovarian carcinoma cells in a single subcutaneous site, on the left axillary flank region of each animal. The tumor injection site was observed twice weekly and measured once palpable. The tumor volume for each mouse was determined by measuring two dimensions with calipers and calculated using the formula: tumor volume=(length× width$^2$)/2). When tumors reached the average volume of approximately 80 mm$^3$, the mice were divided into their respective experimental groups, which consists of vehicle (20 m M sodium phosphate in 0.6% NaCl) controls, Leu-Doxorubicin, compound 1 of Example 1, compound 10 of Example 4, and compound 12 of Example 5). The mice were sorted to evenly distribute tumor size, grouped into 6 mice/cage, and ear punched for permanent identification. Drugs were dosed intravenously via the tail vein once per week for three weeks (Qd7×3). Mouse weight and tumor sizes were measured at the beginning of study and twice weekly through week 5.

The overall growth of tumors was calculated as the mean tumor volume at one week following the end of the treatment. A percent treatment over control (T/C) value was also calculated when the control group's median tumor size reached approximately 800–1100 mm$^3$ and again at one week following treatment. The T/C value in percent is a non-quantitative indication of anti-tumor effectiveness.

Data is presented in Table 2, below.

TABLE 2

PEG-Leu-Doxorubicin Treatment of a Human Ovarian Carcinoma (A2780) Xenograft in Nude Mice$^α$

| Compound | Treatment Schedule (mg/kg/dose) | Tumor Volume (mean ± sem) Day 21 | T/C (%)$^β$ At 1000 mm$^3$ | T/C (%)$^β$ At Day 21 |
| --- | --- | --- | --- | --- |
| Control | 0 | 4238 ± 356 | — | — |
| Leu-Dox | Qd7 × 3 (30) | 659 ± 173 | 26.3 | 19.7 |
| Compound 2 | Qd7 × 3 (30) | 619 ± 231 | 13.2 | 7.4 |
| Compound 10 | Qd7 × 3 (30) | 507 ± 173 | 13.0 | 8.8 |
| Compound 12 | Qd7 × 3 (30) | 379 ± 134 | 14.3 | 6.1 |

$^α$Intravenous treatment in nude mice bearing established tumors (~80 mm$^3$). n = 6/group.
$^β$The median tumor volume of treatment and control groups were measured and compared when the control group's median tumor volume reached approximately 1000 mm$^3$ and one week after final dosage (day 21). T/C < 42% at 1000 mm$^3$ is considered significant anti-tumor activity by the Drug Evaluation Branch of the NCI.

Thus, as can be appreciated from the data presented by Table 2, above, the PEG conjugate forms of leu-doxorubicin were more effective than the non-conjugated parent compound.

Example 9

Synthesis of Compound 19

(Step 1) TFA.Alanine-Camptothecin 18 was prepared as described in commonly assigned U.S. Pat. No. 6,127,355, Example 21, the contents of which are incorporated herein by reference.

(Step 2) 18 (185 mg, 0.36 mmol), was added to solution containing 9 (4 g, 0.0982 mmol) in 50 mL anhydrous methylene chloride and DMAP (49 mg, 0.40 mmol). The mixture was stirred at room temperature overnight. The reaction mixture was evaporated to dryness and the residual solid recrystallized two times from 2-propanol (80 mL) to give pure compound 19 (3.5 g, 86%). $^{13}$C NMR (67.8 MHz, CDCl$_3$) δ170.80, 167.30, 166.08, 156.33, 151.53, 147.99, 146.72, 145.53, 142.07, 133.55, 130.46, 129.61, 129.27, 128.89, 127.94, 127.44, 127.02, 119.09, 107.16, 95.35, 69.74–65.23 (PEG), 59.13, 49.17, 39.32, 30.76, 21.02, 16.45, 15.36, 6.69.

Example 10

Synthesis of Compound 20

TFA.Alanine-Camptothecin (185 mg, 0.36 mmol) 18 was added to a solution of 11 (4.0 g, 0.0983 mmol) in 50 mL anhydrous methylene chloride and DMAP (49 mg, 0.40 mmol). The mixture was stirred at room temperature overnight, the reaction mixture evaporated to dryness, and the residual solid was recrystallized from 2-propanol two times (80 mL) to give pure 20 (3.5 g, 86%). $^{13}$C NMR (67.8 MHz, CDCl$_3$) δ170.83, 166.23, 156.50, 155.21, 152.10, 151.39, 148.20, 145.70, 144.62, 130.75, 130.00, 129.76, 129.04, 128.25, 128.03, 127.54, 127.19, 119.45, 107.70, 95.44, 69.91–65.25 (PEG), 49.31, 44.90, 30.98, 16.82, 15.31, 15.20, 6.81.

Example 11

Synthesis of Compound 21

TFA.Alanine-Camptothecin (102 mg, 0.179 mmol) 18 and DMAP (37 mg, 0.30 mmol) were added to a solution of 5 (2.0 g, 0.0493 mmol) in 40 mL anhydrous methylene chloride. The mixture was stirred at room temperature overnight, the reaction mixture evaporated to dryness, and the residual solid was recrystallized twice from 2-propanol (60 mL) to give pure 21(1.77 g, 87%). $^{13}$C NMR (67.8 MHz, CDCl$_3$) δ171.00, 166.00, 161.07, 156.09, 154.00, 151.00, 148.00, 145.50, 135.75, 130.55, 129.56, 128.81, 127.75, 127.41, 127.02, 126.69, 120.70, 119.00, 107.70, 72.69–67.00 (PEG), 50.70, 48.38, 40.06, 36.86, 30.32, 16.20, 6.65.

Example 12

Synthesis of Compound 22

A solution of compound 4 (5 g, 0.123 mmol) in toluene (75 mL) is azeotroped with the removal of 25 mL of distillate. The reaction mixture is cooled to 30° C., followed by the addition of oxalyl chloride (0.031 g, 0.246 mmol) and one drop of dimethylformamide. This mixture is stirred for 3 hours at 30–40° C., followed by the addition of 2-mercaptothizoline (0.044 g, 0.369 mmol). The reaction mixture is refluxed for 1 hour, followed by filtration and removal of the solvent in vacuo. The crude residue is recrystallized from IPA (100 mL) to yield compound 22 (4 g, 90%). The structure is comfirmed by 13C NMR.

Example 13

Synthesis of Compound 23

Native bovine hemoglobin (bHb) in 100 mM sodium phosphate (pH 8.4)/65 mM NaCl buffer is modified to form the conjugated compound 23 as follows. In a polypropylene container, 20 mL of 22 (0.8 g dissolved in 20 mM sodium phosphate/65 mM NaCl buffer at 4° C.) is added to 20 mL of bHb at 4° C. (22.2 g at 11 mg/mL) with gentle stirring. The pH of the reaction is monitored. The mixture is stirred for 1 hour, the reaction is quenched by the addition of glycine, and stirring is continued for an additional 15 minutes. Cysteine (dissolved in 100 mM sodium phosphate/65 mM NaCl buffer at 4° C., 30 mM final concentration) is added to reduce oxidized hemoglobin (met-Hb) formation, and the reaction mixture is stirred for 16 hours at 4° C. The PEG-Hb is diluted and diafiltered into formulation buffer (5 mM sodium bicarbonate, 4 mM Na$_2$HPO$_4$, 1 mM NaH2PO$_4$, 150 mM NaCl, pH 7.4) to remove the unreacted PEG and/or PEG-glycine conjugate, followed by concentration to 60 mg/mL of compound 23. The purity of the PEG-Hb is determined by size exclusion HPLC.

We claim:

1. A compound of formula I:

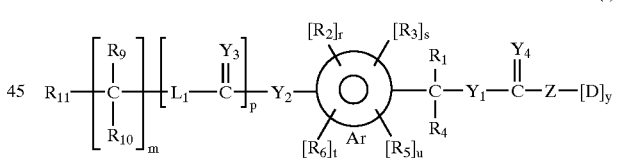

wherein:
- $L_1$ is a bifunctional linking moiety;
- D is a moiety that is a leaving group, or a residue of a compound to be delivered into a cell;
- Z is covalently linked to $[D]_y$, wherein Z is selected from the group consisting of: a moiety that is actively transported into a target cell, a hydrophobic moiety, and combinations thereof;
- $Y_1, Y_2, Y_3$ and $Y_4$ are each independently O, S, or $NR_{12}$;
- $R_{11}$ is a mono- or divalent polymer residue;
- $R_1, R_4, R_9, R_{10}$ and $R_{12}$ are independently selected from the group consisting of hydrogen, $C_{1-6}$ alkyls, $C_{3-12}$ branched alkyls, $C_{3-8}$ cycloalkyls, $C_{1-6}$ substituted alkyls, $C_{3-8}$ substituted cycloalkyls, aryls, substituted aryls, aralkyls, $C_{1-6}$ heteroalkyls, and substituted $C_{1-6}$ hetoroalkyls;
- $R_2, R_3, R_5$ and $R_6$, are independently selected from the group consisting of hydrogen, $C_{1-6}$ alkyls, $C_{1-6}$ alkoxy, phenoxy, $C_{1-8}$ heteroalkyls, $C_{1-8}$ heteroalkoxy, substituted $C_{1-6}$ alkyls, $C_{3-8}$ cycloalkyls, $C_{3-8}$ substituted cycloalkyls, aryls, substituted aryls, aralkyls, halo-, nitro-, cyano-, carboxy-, $C_{1-6}$ carboxyalkyls and $C_{1-6}$ alkylcarbonyls;

Ar is a moiety which when included in Formula (I) forms a multi-substituted aromatic hydrocarbon or a multi-substituted heterocyclic group;

(m), (r), (s), (t), and (u) are independently zero or one;

(p) is zero or a positive integer; and (y) is 1 or 2; wherein $Z[D]_y$ is capable of crossing the membrane of the target cell and is capable of being hydrolyzed therein to release D.

2. The compound of claim 1, wherein $L_1$ is selected from the group consisting of:

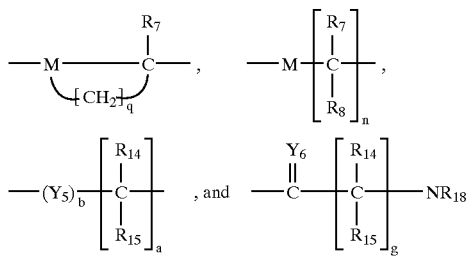

wherein:

M is X or Q; where X is an electron withdrawing group;

Q is a moiety containing a free electron pair positioned three to six atoms from

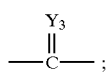

(a) and (n) are independently zero or a positive integer;
(b) is zero or one;
(g) is a positive integer;
(q) is three or four;
$R_7$, $R_8$, $R_{14}$, $R_{15}$ and $R_{18}$ are independently selected from the group which defines $R_9$; and
$Y_5$ and $Y_6$ are independently O, S, or $NR_{12}$.

3. The compound of claim 1 wherein when y is 2, each of the two D moieties is the same or different.

4. The compound of claim 1 wherein Z is selected from the group consisting of an amino acid residue, a sugar residue a fatty acid residue, a peptide residue, a $C_{6-18}$ alkyl, a substituted aryl, a heteroaryl, —C(=O), —C(=S), and —C(=$NR_{16}$), wherein $R_{16}$ is selected from the same group as $R_{12}$.

5. The compound of claim 4 wherein the amino acid residue is selected from the group consisting of alanine, valine, leucine, isoleucine, glycine, serine, threonine, methionine, cysteine, phenylalanine, tyrosine, tryptophan, aspartic acid, glutamic acid, lysine, arginine, histidine and proline.

6. The compound of claim 4 wherein the peptide ranges in size from 2 to about 10 amino acid residues.

7. The compound of claim 6 wherein the peptide is Gly-Phe-Leu-Gly (SEQ ID NO:1) or Gly-Phe-Leu.

8. The compound of claim 1 wherein each D moiety is independently a residue of an active biological material.

9. The compound of claim 1 wherein at least one D moiety is a leaving group selected from the group consisting of N-hydroxybenzotriazolyl, halogen, N-hydroxyphthalimidyl, p-nitrophenoxy, imidazolyl, N-hydroxysuccinimidyl, thiazolidinyl thione, and combinations thereof.

10. The compound of claim 1 wherein Ar is selected from the group consisting of

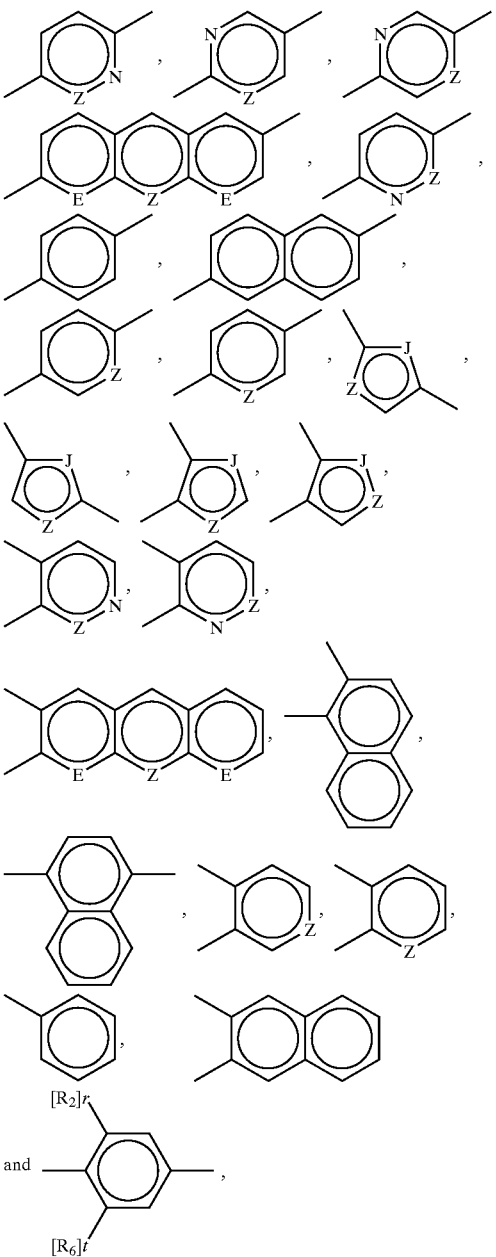

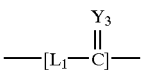

wherein J is selected from the group consisting of O, S, and N—$R_{19}$, B and Z are independently $CR_{19}$ or N—$R_{19}$ and $R_{19}$ is selected from the group consisting of hydrogen, $C_{1-6}$ alkyl, $C_{3-12}$ branched alkyl, $C_{3-8}$ cycloalkyl, $C_{1-6}$ substituted alkyl, $C_{3-8}$ substituted cyoloalkyl, aryls, substituted aryl, aralkyl, $C_{1-6}$ heteroalkyl, and substituted $C_{1-6}$ heteroalkyls.

11. The compound of claim 1, wherein $$-[L_1-\overset{\overset{Y_3}{\|}}{C}]-$$

comprises an amino acid residue.

12. The compound of claim 11, wherein said amino acid residue is selected from the group consisting of naturally occurring and non-naturally occurring amino acid residues.

13. The compound of claim 1, wherein (p) is one.

14. The compound of claim 2, wherein X is selected from the group consisting of O and $NR_{12}$.

15. The compound of claim 2, wherein Q is selected from the group consisting of $C_{2-4}$ alkyls, cycloalkyls, aryls, and aralkyl groups substituted with a member of the group consisting of NH, O, S, —$CH_2$—C(O)—N(H)—, and ortho-substituted phenyls.

16. The compound of claim 2, wherein (n) is 1 or 2.

17. The compound of claim 1, wherein (m) is 0.

18. The compound of claim 1, wherein $Y_1, Y_2, Y_3$ and $Y_4$ are O.

19. The compound of claim 1, wherein $R_{11}$ comprises a polyalkylene oxide residue.

20. The compound of claim 19, wherein said polyalkylene oxide residue comprises polyethylene glycol.

21. The compound of claim 1 wherein said polymer residue has a number average molecular weight of from about 2000 to about 100,000 daltons.

22. The compound of claim 1, wherein said polymer residue has a number average molecular weight of from about 20,000 to about 40,000 daltons.

23. The compound of claim 10, wherein Ar is

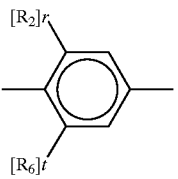

wherein r and t are both 1, $R_2$ and $R_6$ are independently H or methyl.

24. The compound of claim 1 that is selected from the group consisting of:

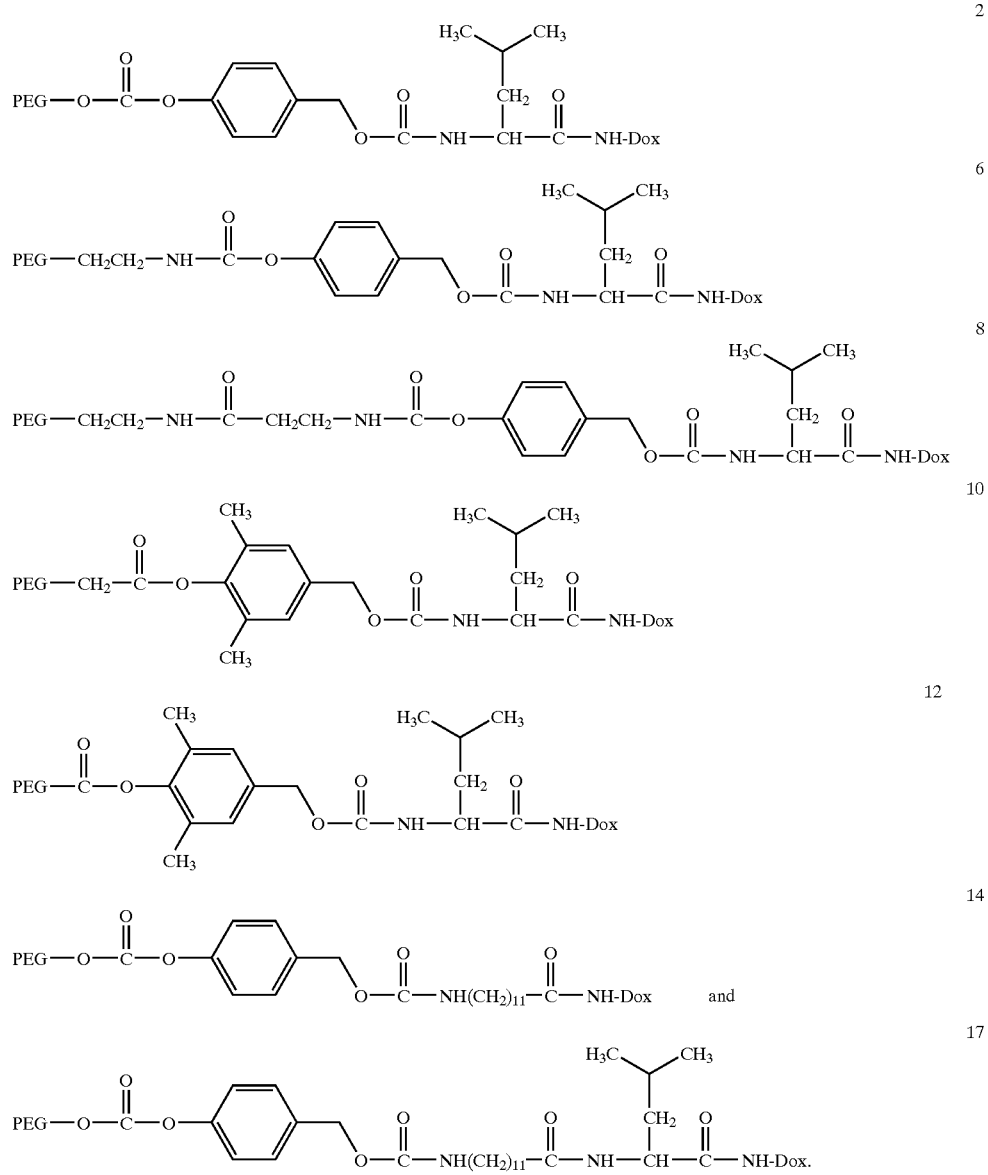

25. The compound of claim 24 wherein the polyethylene glycol (PEG) has a number average molecular weight of from about 20,000 to about 40,000 daltons.

26. A composition comprising a pharmaceutically or diagnostically effective amount of the compound of claim 1, where D is a residue of a compound to be delivered into a cell, together with a carrier acceptable for in vivo administration to an animal in need thereof.

27. A method of treating a disease or disorder in an animal, that comprises administering a pharmaceutically acceptable composition comprising an effective amount of a compound of claim 1, where D is a moiety that is a residue of a compound to be delivered into a cell; to an animal in need thereof.

28. A method of delivering a biologically active material D into a cell in need of treatment therewith, comprising the process of administering a compound of claim 1 to an animal comprising said cell, wherein Formula I is hydrolyzed in vivo extracellularly to yield:

Formula I-(i)

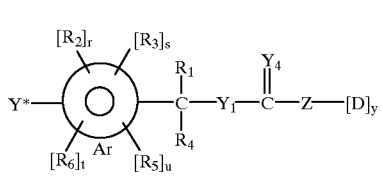

wherein Y* is the remainder of $Y_2$, and is independently selected from the group consisting of HO—, HS—, or $HNR_{12}$;

and Formula I-(i) then spontaneously hydrolyzes to

Formula I-(ii)

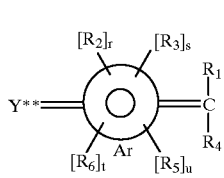

and $CO_2$, and a compound of Formula I-(iii) Z—$[D]_y$ is released;

wherein Y** is the remainder of Y*, and is independently selected from the group consisting of O, S, or $NR_{12}$; and Z—$[D]_y$ crosses the membrane of the cell, and is hydrolyzed therein to release D.

29. The compound of claim 2, wherein X is selected from the group consisting of O, $NR_{12}$,

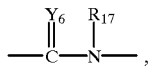

S, SO and $SO_2$ where $R_{17}$ is independently selected from the group consisting of hydrogen, $C_{1-6}$ alkyls, $C_{3-12}$ branched alkyls, $C_{3-8}$ cycloalkyls, $C_{1-6}$ substituted alkyls, $C_{3-8}$ substituted cycloalkyls, aryls, substituted aryls, aralkyls, $C_{1-6}$ heteroalkyls, and substituted $C_{1-6}$ heteroalkyls.

30. A compound of Formula I:

(I)

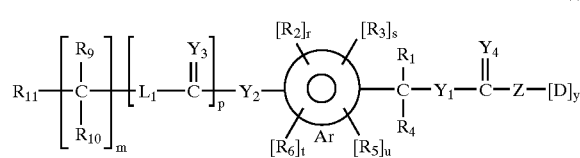

wherein:
$L_1$ is a bifunctional linking moiety;
each D moiety is independently a residue of an anticancer agent, an anticancer prodrug, a detectable tag, or combinations thereof;
Z is covalently linked to $[D]_y$, wherein Z is selected from the group consisting of: a moiety that is actively transported into a target cell, a hydrophobic moiety, and combinations thereof;
$Y_1$, $Y_2$, and $Y_4$ are each independently O, S, or $NR_{12}$;
$R_{11}$ is a mono- or divalent polymer residue;
$R_1$, $R_4$, $R_9$, $R_{10}$ and $R_{12}$ are independently selected from the group consisting of hydrogen, $C_{1-6}$ alkyls, $C_{3-12}$ branched alkyls, $C_{3-8}$ cycloalkyls, $C_{1-6}$ substituted alkyls, $C_{3-8}$ substituted cycloalkyls, aryls, substituted aryls, aralkyls, $C_{1-6}$ heteroalkyls, and substituted $C_{1-6}$ heteroalkyls;
$R_2$, $R_3$, $R_5$ and $R_6$ are independently selected from the group consisting of hydrogen, $C_{1-6}$ alkyls, $C_{1-6}$ alkoxy, phenoxy, $C_{1-8}$ heteroalkyls, $C_{1-8}$ heteroalkoxy, substituted $C_{1-6}$ alkyls, $C_{3-8}$ cyoloalkyls, $C_{3-8}$ substituted cycloalkyls, aryls, substituted aryls, aralkyls, halo-, nitro-, cyano-, carboxy-, $C_{1-6}$ carboxyalkyls and $C_{1-6}$ alkylcarbonyls;
Ar is a moiety which when included in Formula (V) forms a multi-substituted aromatic hydrocarbon or a multi-substituted heterocyclic group;
(m), (r), (s), (t), and (u) are independently zero or one;
(p) is zero or a positive integer;

31. The compound of claim 30 wherein the anticancer agent or anticancer prodrug comprises an anthracycline compound or a topoisomerase T inhibitor.

32. The compound of claim 30 wherein the anticancer agent or anticancer prodrug is selected from the group consisting of daunorubicin, doxorubicin, p-aminoaniline mustard, melphalan, cytosine arabinoside, gemcitabine, and combinations thereof.

33. A method of preparing a tetrapartate prodrug comprising reacting a compound of formula:

III

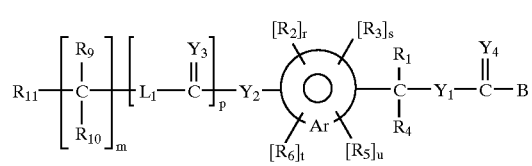

with a compound of formula:

Lx—Z—$[D]_y$;  IV wherein B is a leaving group for Formula III;
$L_1$ is a bifunctional linking moiety;
D is a moiety that is a leaving group, or a residue of a compound to be delivered into a cell;

Lx is a leaving group for Formula IV;

Z is covalently linked to [D]$_y$, wherein Z is selected from the group consisting of: a moiety that is actively transported into a target cell, a hydrophobic moiety, and combinations thereof;

$R_1$, $R_4$, $R_9$, $R_{10}$ and $R_{12}$ are independently selected from the group consisting of hydrogen, $C_{1-6}$ alkyls, $C_{3-12}$ branched alkyls, $C_{3-8}$ cycloalkyls, $C_{1-6}$ substituted alkyls, $C_{3-8}$ substituted cycloalkyls, aryls, substituted aryls, aralkyls, $C_{1-6}$ heteroalkyls, and substituted $C_{1-6}$ heteroalkyls;

$R_2$, $R_3$, $R_5$, and $R_6$ are independently selected from the group consisting of hydrogen, $C_{1-6}$ alkyls, $C_{1-6}$ alkoxy, phenoxy, $C_{1-8}$ heteroalkyls, $C_{1-8}$ heteroalkoxy, substituted $C_{1-6}$ alkyls, $C_{3-8}$ cycloalkyls, $C_{3-8}$ substituted cycloalkyls, aryls, substituted aryls, aralkyls, halo-, nitro-, cyano-, carboxy-, $C_{1-6}$ carboxyalkyls and $C_{1-6}$ alkylcarbonyls;

Ar is a moiety which when included in Formula (III) forms a multi-substituted aromatic hydrocarbon or a multi-substituted heterocyclic group;

(m), (r), (s), (t), and (u) are independently zero or one;

(p) is zero or a positive integer, (y) is one or two;

$Y_1$, $Y_2$, $Y_3$ and $Y_4$ are each independently O, S, or $NR_{12}$; and $R_{11}$ is a monovalent or divalent polymer residue.

34. A method of preparing a tetrapartate prodrug comprising reacting a compound of formula

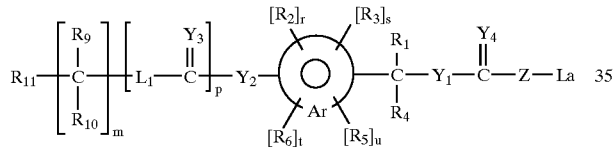

V with at least one biologically active material; wherein $L_1$ is a bifunctional linking moiety;

La is a leaving group for Formula V;

Z is covalently linked to La and wherein Z is selected from the group consisting of: a moiety that is actively transported into a target cell, a hydrophobic moiety, and combinations thereof;

$R_1$, $R_4$, $R_9$, $R_{10}$ and $R_{12}$ are independently selected from the group consisting of hydrogen, $C_{1-6}$ alkyls, $C_{3-12}$ branched alkyls, $C_{3-8}$ cycloalkyls, $C_{1-6}$ substituted alkyls, $C_{3-8}$ substituted cyoloalkyls, aryls, substituted aryls, aralkyls, $C_{1-6}$ heteroalkyls, and substituted $C_{1-6}$ heteroalkyls;

$R_2$, $R_3$, $R_5$ and $R_6$ are independently selected from the group consisting of hydrogen, $Y_1$, $Y_2$, $Y_3$ and $Y_4$ are independently O, S, or $NR_{12}$; and $R_{11}$ is a monovalent or divalent polymer residue wherein after the reaction Z is covalently linked to the at least one biologically active material.

35. A compound of Formula I:

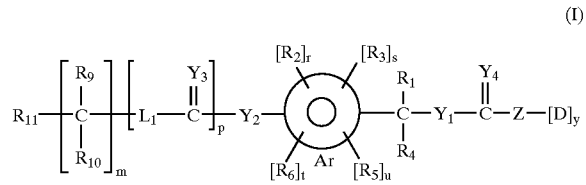

(I)

wherein:

$L_1$ —C(=$Y_3$) comprises an amino acid residue;

D is a moiety that is a leaving group, or a residue of a compound to be delivered into a cell;

Z is covalently linked to [D]$_y$, wherein Z is selected from the group consisting of: a moiety that is actively transported into a target cell, a hydrophobic moiety, and combinations thereof;

$Y_1$, $Y_2$ and $Y_4$ are each independently O, S, or $NR_{12}$;

$R_{11}$ is a mono- or divalent polymer residue;

$R_1$, $R_4$, $R_9$, $R_{10}$ and $R_{12}$ are independently selected from the group consisting of hydrogen, $C_{1-6}$ alkyls, $C_{3-12}$ branched alkyls, $C_{3-8}$ cycloalkyls, $C_{1-6}$ substituted alkyls, $C_{3-8}$ substituted cyoloalkyls, aryls, substituted aryls, aralkyls, $C_{1-6}$ heteroalkyls, and substituted $C_{1-6}$ heteroalkyls;

$R_2$, $R_3$, $R_5$ and $R_6$ are independently selected from the group consisting of hydrogen, $C_{1-6}$ alkyls, $C_{1-6}$ alkoxy, phenoxy, $C_{1-8}$ heteroalkyls, $C_{1-8}$ heteroalkoxy, substituted $C_{1-6}$ alkyls, $C_{3-8}$ cycloalkyls, $C_{3-8}$ substituted cycloalkyls, aryls, substituted aryls, aralkyls, halo-, nitro-, cyano-, carboxy-, $C_{1-6}$ carboxyalkyls and $C_{1-6}$ alkylcarbonyls;

Ar is a moiety which when included in Formula (I) forms a multi-substituted aromatic hydrocarbon or a multi-substituted heterocyclic group;

(m), (r), (s), (t), and (u) are independently zero or one; and (p) is zero or a positive integer; and (y) is 1 or 2.

* * * * *

UNITED STATES PATENT AND TRADEMARK OFFICE
CERTIFICATE OF CORRECTION

PATENT NO.   : 6,720,306 B2
DATED        : April 13, 2004
INVENTOR(S)  : Greenwald, R.B. et al.

It is certified that error appears in the above-identified patent and that said Letters Patent is hereby corrected as shown below:

Column 33,
Lines 46-47, "a sugar residue a fatty acid residue" should read -- a sugar residue, a fatty acid residue --;

Column 34,
Lines 41-44, the first compound should appear as follows: 
Line 53, "B" should read -- E --;
Line 56 "cyoloalkyl" should read -- cycloalkyl --;

Column 38,
Line 40, "(p) is zero or a positive integer;" should read -- (p) is zero or a positive integer; and (y) is 1 or 2. --;

Column 39,
Line 27, "$R_{11,}$" should read -- $R_{11}$ --; and

Column 40,
Line 2, "group consisting of hydrogen" should read -- group consisting of hydrogen, $C_{1-6}$ alkyls, $C_{1-6}$ alkoxy, phenoxy, $C_{1-8}$ heteroalkyls, $C_{1-8}$ heteroalkoxy, substituted $C_{1-6}$ alkyls, $C_{3-8}$ cycloalkyls, $C_{3-8}$ substituted cycloalkyls, aryls, substituted aryls, aralkyls, halo-, nitro-, cyano-, carboxy-, $C_{1-6}$ carboxyalkyls and $C_{1-6}$ alkylcarbonyls; Ar is a moiety which when included in Formula (V) forms a multi-substituted aromatic hydrocarbon or a multi-substituted heterocyclic group; (m), (r), (s), (t), and (u) are independently zero or one; (p) is zero or a positive integer --.

Signed and Sealed this

First Day of February, 2005

JON W. DUDAS
*Director of the United States Patent and Trademark Office*

SEQUENCE LISTING

```
<160> NUMBER OF SEQ ID NOS: 1

<210> SEQ ID NO 1
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide linker

<400> SEQUENCE: 1

Gly Phe Leu Gly
1
```